(12) United States Patent
Söderpalm et al.

(10) Patent No.: US 11,318,143 B2
(45) Date of Patent: May 3, 2022

(54) TREATMENT OF ALCOHOL USE DISORDER

(71) Applicants: Bo Söderpalm, Bollebygd (SE);
Andrea De Bejczy, Gothenburg (SE)

(72) Inventors: Bo Söderpalm, Bollebygd (SE);
Andrea De Bejczy, Gothenburg (SE)

( * ) Notice: Subject to any disclaimer, the term of this patent is extended or adjusted under 35 U.S.C. 154(b) by 0 days.

(21) Appl. No.: 16/484,432

(22) PCT Filed: Feb. 16, 2018

(86) PCT No.: PCT/EP2018/053914
§ 371 (c)(1),
(2) Date: Aug. 7, 2019

(87) PCT Pub. No.: WO2018/149979
PCT Pub. Date: Aug. 23, 2018

(65) Prior Publication Data
US 2020/0009153 A1  Jan. 9, 2020

(30) Foreign Application Priority Data
Feb. 17, 2017 (GB) .................................... 1702590

(51) Int. Cl.
*A61K 31/55* (2006.01)
*A61K 31/137* (2006.01)

(52) U.S. Cl.
CPC ............ *A61K 31/55* (2013.01); *A61K 31/137* (2013.01)

(58) Field of Classification Search
CPC ............................... A61K 31/55; A61K 31/137
See application file for complete search history.

(56) References Cited

U.S. PATENT DOCUMENTS

2006/0084656 A1  4/2006  Ziegler et al.
2009/0017102 A1  1/2009  Stinchcomb et al.

OTHER PUBLICATIONS

Rose, Jed et al, Am J Psychiatry (2014), vol. 171 (11), pp. 1199-1205. (Year: 2014).*
Ebbert et al, Nicotine & Tobacco Reserach (2009), vol. 11 (3), pp. 234-239. (Year: 2009).*
McKee et al, Biol Psychiatry (2009), vol. 66, pp. 185-190. (Year: 2009).*
Berigan et al, Timothy R., D.D.S., M.D., Bupropion Related Alcohol Cessation, Internet Archive, 2017, web.archive.org, Available from https://web.archive.Org/web/20151004195628/http://www.priory.com/psych/bupropion.htm [Accessed Jan. 25, 2019]. (Year: 2015).*
Berigan, Timothy R., D.D.S., M.D., Bupropion Related Alcohol Cessation, Internet Archive, 2017, web.archive.org, Available from https://web.archive.org/web/20151004195628/http://www.priory.com/psych/bupropion.htm [Accessed Jan. 25, 2019].

(Continued)

*Primary Examiner* — Craig D Ricci
*Assistant Examiner* — Janet L Coppins
(74) *Attorney, Agent, or Firm* — Porter Wright Morris & Arthur LLP

(57) ABSTRACT

The present invention is directed to a combination of varenicline and bupropion for use in treating alcohol use disorder (AUD) and/or treating alcohol risk consumption in a subject in need thereof. Corresponding compositions, uses and methods of treatment are also provided.

10 Claims, 3 Drawing Sheets

(56) References Cited

OTHER PUBLICATIONS

Ebbert, Jon O. et al., Varenicline and bupropion sustained-release combination therapy for smoking cessation, Nitcotine & Tobacco Research, vol. 11, No. 3, pp. 234-239 (2009).

Ebbert, Jon O. et al., Combination Varenicline and Bupropion SR for Tobacco Dependence Treatment in Cigarette Smokers: A Randomized Trial, JAMA, vol. 311, No. 2, pp. 155-163 (2014).

Hall, Brandon J. et al., Bupropion-Varenicline Interactions and Nicotine Self-Administration Behavior in Rats, Pharmacol Biochem Behav., vol. 130, pp. 84-89 (2015) (Author Manuscript, pp. 1-15).

Hong, MD, Arthur et al., Depressive Symptoms Among Patients Receiving Varenicline and Bupropion for Smoking Cessation, J Subst Abuse Treat., vol. 52, pp. 78-81 (2015).

Issa, Jaqueline S. et al., Effectiveness of Coadministration of Varenicline, Bupropion, and Serotonin Reuptake Inhibitors in a Smoking Cessation Program in the Real-Life Setting, Nicotine & Tobacco Research, vol. 15, No. 6, pp. 1146-1150 (2013) (Online, pp. 1-6 (2012)).

Karam-Hage, MD, Maher et al., Addition of Bupropion SR to Varenicline Alleviated Depression and Suicidal Ideation: A Case Report, Prim Care Companion J Clin Psychiatry, vol. 12, No. 2, pp. 1-2 (2010).

McKee, Sherry A. et al., Varenicline Reduces Alcohol Self-Administration in Heavy-Drinking Smokers, Biol Psychiatry, vol. 66, No. 2, pp. 185-190 (2009).

Plebani, Jennifer G. et al., Results from a pilot clinical trial of varenicline for the treatment of alcohol dependence, Drug Alcohol Depend., vol. 133, No. 2, pp. 754-758 (2013) (Author Manuscript, pp. 1-15).

Rose, Jed E. et al., Combination Varenicline/Bupropion Treatment in an Adaptive Smoking Cessation Paradigm, Am J Psychiatry, vol. 171, No. 11, pp. 1199-1205 (2014).

Schacht, Joseph P. et al., Varenicline effects on drinking, craving and neural reward processing among non-treatment-seeking alcohol-dependent individuals, Psychopharmacology, vol. 231, No. 18, pp. 3799-3807 (2014) (Author Manuscript, pp. 1-19).

Wellbutrin and cravings, soberrecovery.com, Available at https://www.soberrecovery.com/forums/alcoholism/295417-wellbutrin-cravings.html, pp. 1-9, (May 21, 2013) [Accessed Jan. 25, 2019].

Karam-Hage, Maher et al., Bupropion-SR for Smoking Cessation in Early Recovery from Alcohol Dependence: A Placebo-Controlled, Double-Blind Pilot Study, Am J Drug Alcohol Abuse, vol. 37, No. 6, pp. 487-490 (Nov. 2011).

Zhang, Kaiwu, A comparative study of effect of bupropion on symptoms of patients with alcohol dependence, Journal of Psychiatry, vol. 26, No. 6, pp. 439-441 (2013), and English Abstract.

\* cited by examiner

TREATMENT OF ALCOHOL USE DISORDER

The present invention is directed to a combination of varenicline and bupropion for use in treating alcohol use disorder (AUD) and/or treating alcohol risk consumption in a subject in need thereof. Corresponding compositions, uses and methods of treatment are also provided.

BACKGROUND

According to the World Health Organization (WHO), alcohol use disorder (AUD) is the fourth largest contributor to global burden of disease, contributing approximately 8% to the total disease burden (WHO, 2014). In Sweden, there are an estimated 330000 alcoholics and approximately 700000 individuals with risky alcohol consumption levels (CAN, 2014). Thus, a million people in Sweden alone are at increased medical risk due to their alcohol consumption, with the total annual financial cost to Swedish society being estimated as 26-100 billion Swedish Krona (Johnson, 2000). Life-time expectancy of individuals afflicted with AUD is shortened by approximately 20 years (Lesch et al., 1986) and the life-time risk of dying from alcohol-related causes (such as accidents and diseases) increases exponentially with alcohol consumption (Nutt & Rehm, 2014; Rehm, 2011). Modest reductions of alcohol intake can therefore dramatically lower the risk of death in the heaviest consumers (Nutt & Rehm, 2014; Rehm & Roerecke, 2013). For this reason, the objective of AUD treatment has recently shifted from abstinence to a reduction in alcohol consumption to lower risk levels. This shift in focus takes into consideration that many patients with AUD are not motivated to abstain from alcohol but may be willing to reduce their intake (Heather, Adamson, Raistrick, Slegg, & Team, 2010; Hodgins, Leigh, Milne, & Gerrish, 1997). In fact, many patients with AUD express a wish to be able to drink alcohol in a controlled, recreational manner, equivalent to people without AUD.

Both psychological and pharmacological treatment options are available for AUD (Socialstyrelsen, 2015). However, the effect sizes are small and the frustration is large among patients, doctors and significant others when trying to combat the disorder. Four medications are available on the Swedish market—disulfiram (Antabus®), acamprosate, naltrexone and nalmefene, of which the latter is non-reimbursed. Disulfiram has a good effect short-term, but only for patients accepting the abstinence goal, since its effect builds on the disulfiram-ethanol effect, causing aversive and potentially harmful somatic reactions due to acetaldehyde intoxication. However, disulfiram has no effect on alcohol craving and compliance to unsupervised treatment is low. In addition, disulfiram is liver toxic and cannot be administered to alcohol dependent subjects with liver impairment (which accounts for approximately 30% of alcohol dependent subjects) (Diehl et al., 2010; Jorgensen, Pedersen, & Tonnesen, 2011; Laaksonen, Koski-Jannes, Salaspuro, Ahtinen, & Alho, 2008). Naltrexone, approved in the 1990's, has its main effect on alcohol craving and prevention of heavy drinking. Numbers-needed-to-treat (NNT) is calculated to 8.6 and the effect size to Cohen's D of 0.2 (Maisel, Blodgett, Wilbourne, Humphreys, & Finney, 2013; Spagnolo et al., 2014; Zindel & Kranzler, 2014). Acamprosate, approved in 2004, also asserts its effects mainly on alcohol craving and prevention of relapse with Cohen's D effect size of 0.32 and NNT calculated to 7.5 (Maisel et al., 2013; Zindel & Kranzler, 2014). There is unfortunately a tendency to develop tolerance against the alcohol reducing effects of acamprosate (Lido, Marston, Ericson, & Soderpalm, 2012). The fourth pharmacological treatment option is Nalmefene, a substance closely related to Naltrexone. Nalmefene can be used in an on-demand strategy and is approved for adult high consuming (over 60 grams/day for males and 40 grams/day for women) alcohol dependent patients. There are no figures for efficacy numbers but they are considered to be in the same range as Naltrexone (Donoghue et al., 2015; Palpacuer et al., 2015).

European GPs, internists and psychiatrists currently prescribe these drugs in modest amounts and the treatment gap has been estimated to be over 90% (Kohn, Saxena, Levav, & Saraceno, 2004). The reason for this is unknown, but with an overall numbers needed to treat (NNTs) of approximately 8-14 (Jonas et al., 2014; Soyka & Chick, 2003; Srisurapanont & Jarusuraisin, 2002), the drugs currently on the market may incorrectly be perceived as useless.

There is a clear need for new treatment options for AUD and/or alcohol risk consumption with considerably larger effect sizes and lower NNTs. Such treatment options would most likely stand a better chance in gaining acceptance amongst practitioners and thus would be more effective in the treatment of this much at risk patient population.

BRIEF SUMMARY OF THE DISCLOSURE

The inventors have been investigating novel treatment regimens for alcohol use disorder (AUD) and/or alcohol risk consumption (ARC). Based on their personal insight of the medication available, its mechanism of action, and its interaction with the complex signalling pathways involved in the reward pathway, the inventors have identified a new treatment option for AUD and/or ARC.

A novel combination of varenicline and bupropion is provided for use in treating alcohol use disorder and/or alcohol risk consumption in a subject in need thereof. Corresponding compositions, uses and methods are also provided.

The invention was conceived due to the inventors' unique in-depth translational knowledge of both the pharmacology and clinical presentation of both nicotine and alcohol dependency and a leap of mind.

Bupropion has been available as a pharmacotherapy for decades, and for smoking cessation since 2000 (Zyban®, EMA). Despite this there is no trial available or listed in Government Research Trials examining whether or not it by itself or in combination with varenicline (registered for smoking cessation 2006 (Champix®, EMA)), would be beneficial in the treatment of AUD. Further, there are no animal data available, besides that provided herein, exploring whether the combination of bupropion and varenicline influences alcohol intake.

The beneficial effects observed herein when varenicline and bupropion are combined are not obvious for at least the following five reasons:

1) Nicotine and ethanol dependence are two distinct entities, classified as two different psychiatric disorders according to DSM-V and ICD-10. Although often associated in epidemiological studies, so are nicotine dependence and opiate dependence, nicotine dependence and amphetamine dependence, nicotine dependence and depression, nicotine dependence and schizophrenia and nicotine dependence and ADHD. Despite this, disorders often associated in epidemiological studies cannot be expected to respond favourably to the same medications. Schizophrenia, for example, would be expected to be worsened by adding bupropion to varenicline. Conversely, pharmacotherapies available for treating AUD, acamprosate and naltrexone, have been tried on nicotine dependence but show no effect on this condition. The beneficial effect observed herein when bupropion is used in combination with varenicline is therefore unexpected.

2) Ethanol and nicotine are very different drugs with different primary mechanisms of action and produce their effects in completely different dose ranges (nicotine in the nM range and ethanol in the mM range). The pharmacodynamic effects of nicotine and ethanol are also very different. Nicotine is considered a mild central stimulant whereas ethanol is classified as a sedative. Depending on dose, ethanol may produce inebriation, intoxication, sedation, cognitive impairment, pro-aggressive effects, lack of judgement, motor in-coordination/ataxia, sleep and, finally, death by respiratory depression, none of which is observed after nicotine. After long-term consumption of large amounts of ethanol a life-threatening withdrawal syndrome may occur, which is not observed after nicotine.

Nicotine produces its effects by directly interfering with a family of receptors for the neurotransmitter acetylcholine (nicotinic acetylcholine receptors (nAChRs)) and secondarily affects extracellular levels of various neurotransmitters in the brain. All central effects of nicotine can efficiently be counteracted by blocking central nAChRs by the unspecific nicotinic receptor antagonist mecamylamine.

Ethanol, on the other hand, has no receptor of its own but directly interferes with a number of proteins that can affect neuronal excitability, among them ligand-gated ion-channels ($GABA_A$-receptors, NMDA receptors, strychnine-sensitive glycine receptors, $5-HT_3$ receptors, and some nAChRs), and in addition with L-type $Ca^{2+}$ ion channels and G protein-activated inwardly rectifying $K^+$ channels. These interactions can in turn change the extracellular levels of various neurotransmitters. Further, there is no single receptor active agent that can block all the pharmacodynamic effects of ethanol. Thus, ethanol's pharmacology is far more complex than nicotine's and only some of ethanol's pharmacodynamic actions may be influenced by nicotinic antagonists.

The predominant theories as regards the dependence producing and addictive effects of ethanol are that they involve the drug's interaction with GABA ($GABA_A$ receptors) and glutamate systems (NMDA receptors) and that corticotropin releasing hormone (and the CRH1 receptor) is involved, whereas others claim that brain dopamine systems may be involved. However, how ethanol interacts with the dopamine system is a matter of controversy where a number of researchers argue that metabolites of ethanol rather than ethanol itself interfere with the dopamine system, and others state that ethanol interferes with this system via liberation of endogenous opioids. Yet others suggest that the interaction is due to ethanol's $GABA_A$-mediated effects. The inventors have developed the concept that ethanol's dopamine activation involves nAChRs, but this is not the predominant theory in the literature.

3) The genetic risk factors for nicotine dependence and alcohol dependence are separate, and are for example related to the specific drugs' metabolism, which differs distinctly.

4) Bupropion and varenicline both interact with brain dopamine systems but their mechanisms of action are very different. Varenicline interacts directly with nAChR located on dopamine neurons, both on the cell-bodies and on the neuronal terminals. The interaction with receptors on the dopamine cell-bodies will increase the cell-firing and thereby the impulse-driven dopamine release from the neuronal terminals. The interaction with nAChRs on the terminals will also facilitate dopamine release. Varenicline is a partial agonist meaning that it will not produce a full effect in these receptors, as would nicotine, but it will instead block further nAChR activation by nicotine, since it has a higher affinity for the receptor than nicotine. Varenicline also interacts with subtypes of nAChRs that ethanol is supposed to indirectly interact with, and according to some studies it therefore also prevents dopamine activation and the associated "high" produced by ethanol.

Bupropion instead blocks dopamine reuptake transporters (as well as noradrenaline transporters) located both on dopamine neuronal cell-bodies and on dopamine neuronal terminals. When these transporters are blocked dopamine that has been released from the dopamine cells, both at terminals and at the cell-bodies (so-called somatodendritic release), will be prevented from reuptake to the dopamine neurons. This will increase extracellular levels of dopamine. In the cell-body region these enhanced extracellular levels of dopamine will activate somatodendritically located dopamine autoreceptors which will lead to reduced dopamine neuronal firing and thereby reduced dopamine release from the neuronal terminals.

When co-administering varenicline and bupropion an additive effect on extracellular dopamine levels in the terminal region is produced (see results). This is probably explained by at least two mechanisms, 1) that the dopamine release produced by varenicline via increased neuronal firing is enhanced by prevention of reuptake of the released dopamine, and 2) that the dopamine autoreceptor mediated decrease of neuronal firing produced by bupropion is overridden by nAChR-induced stimulation of neuronal firing.

5) Nicotine dependence is not to the same extent characterized by the loss of control and binge consumption as is alcohol dependence and also nicotine consumption has not the major impact on life quality and behavioral changes as has alcohol consumption. This difference is for example a major difference in diagnostics and for treatment strategies and a reason why the well-used substitution therapy with nicotine is not naturally considered for AUD.

In one aspect, the invention provides a combination comprising an effective amount of varenicline and an effective amount of bupropion for use in treating alcohol use disorder and/or treating alcohol risk consumption in a subject in need thereof.

In another aspect, the invention provides a composition comprising an effective amount of varenicline for use in treating alcohol use disorder and/or treating alcohol risk consumption in a subject in need thereof in combination with a composition comprising an effective amount of bupropion.

In another aspect, the invention provides a composition comprising an effective amount of bupropion for use in treating alcohol use disorder and/or treating alcohol risk consumption in a subject in need thereof in combination with a composition comprising an effective amount of varenicline.

In another aspect, the invention provides the use of a combination comprising an effective amount of varenicline and an effective amount of bupropion in the manufacture of a medicament for the treatment of alcohol use disorder and/or treatment of alcohol risk consumption in a subject in need thereof.

Suitably, varenicline and bupropion may be provided in a form which is suitable for sequential, separate and/or simultaneous administration.

In another aspect, the invention provides a method of treating alcohol use disorder and/or treating alcohol risk consumption in a subject in need thereof, comprising administering to the subject a combination of an effective amount of varenicline and an effective amount of bupropion.

In another aspect, the invention provides a method of treating alcohol use disorder and/or treating alcohol risk consumption in a subject in need thereof, comprising administering to the subject an effective amount of varenicline, wherein the subject is undergoing treatment with an effective amount of bupropion.

In another aspect, the invention provides a method of treating alcohol disorder and/or treating alcohol risk consumption in a subject in need thereof, comprising administering to the subject an effective amount of bupropion, wherein the subject is undergoing treatment with an effective amount of varenicline.

Suitably, varenicline and bupropion are administered sequentially, separately and/or simultaneously.

Suitably, the effective amount of varenicline is in the range of from about 0.1 mg/day to about 5 mg/day, optionally wherein the effective amount of varenicline is in the range of from about 0.5 mg/day to about 2 mg/day.

Suitably, the effective amount of bupropion is in the range of from about 25 mg/day to about 600 mg/day, optionally wherein the effective amount of bupropion is in the range of from about 150 mg/day to about 300 mg/day.

Suitably, the subject is human.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The patent, scientific and technical literature referred to herein establish knowledge that was available to those skilled in the art at the time of filing. The entire disclosures of the issued patents, published and pending patent applications, and other publications that are cited herein are hereby incorporated by reference to the same extent as if each was specifically and individually indicated to be incorporated by reference. In the case of any inconsistencies, the present disclosure will prevail.

Various aspects of the invention are described in further detail below.

BRIEF DESCRIPTION OF THE DRAWINGS

Embodiments of the invention are further described hereinafter with reference to the accompanying drawing, in which:

FIG. 5 illustrates the Area Under the Curve (AUC) 0-140 minutes (Bup 5 vs Var+Bup 5: $p<0.001$.

DETAILED DESCRIPTION

Figure 1:
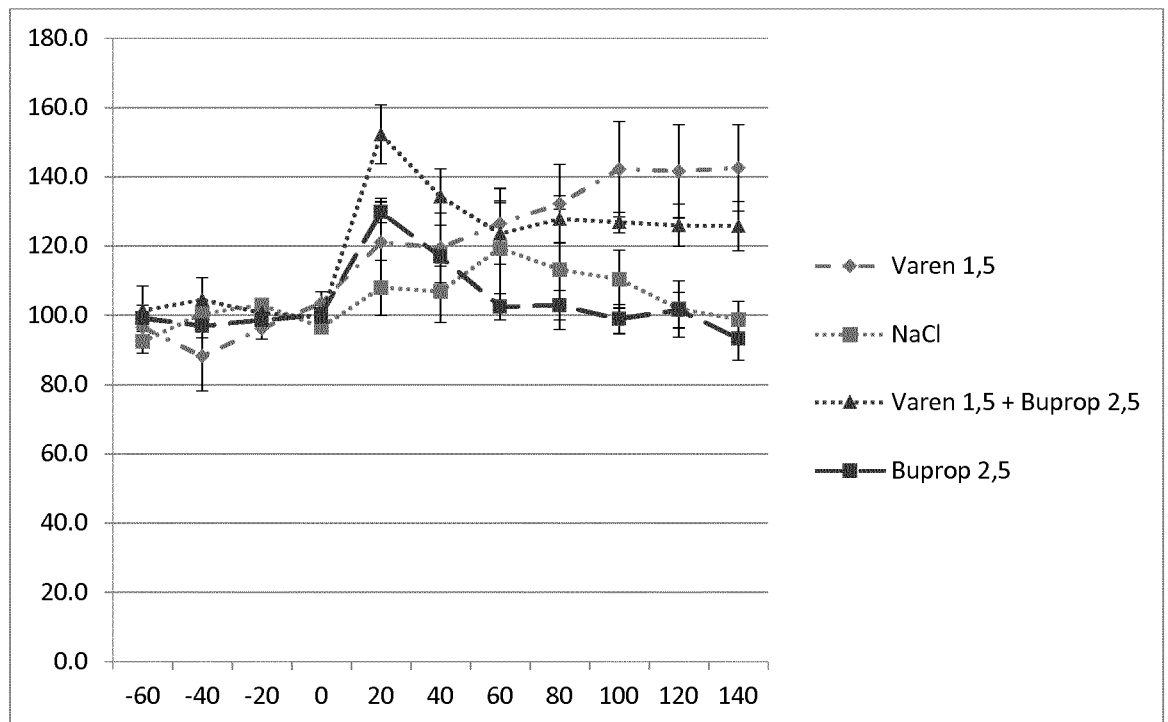
FIG. 1 demonstrates that the addition of bupropion boosts the increased dopamine output in the rat nucleus accumbens induced by varenicline. Shown are dopamine levels measured in the dialysate expressed as percent of baseline. Drugs (mg/kg) or control solution (NaCl) was injected i.p. directly after time-point 0.
Figure 2:
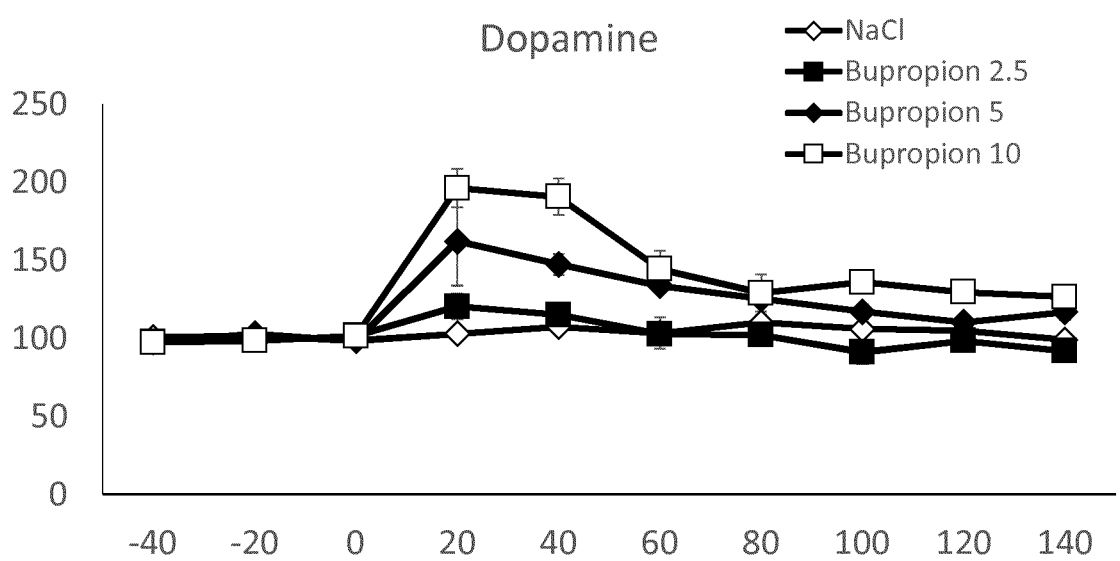
FIGS. 2 and 3 show results from in vivo microdialysis in the nucleus accumbens in awake freely moving male Wistar rats after injection of varenicline (1.5 mg/kg, i.p.) or bupropion (2.5, 5 and 10 mg/kg i.p.) Dopamine levels in the dialysate are expressed as percent of baseline. Drugs or control solution (NaCl) was injected directly after time-point 0.
Figure 3:
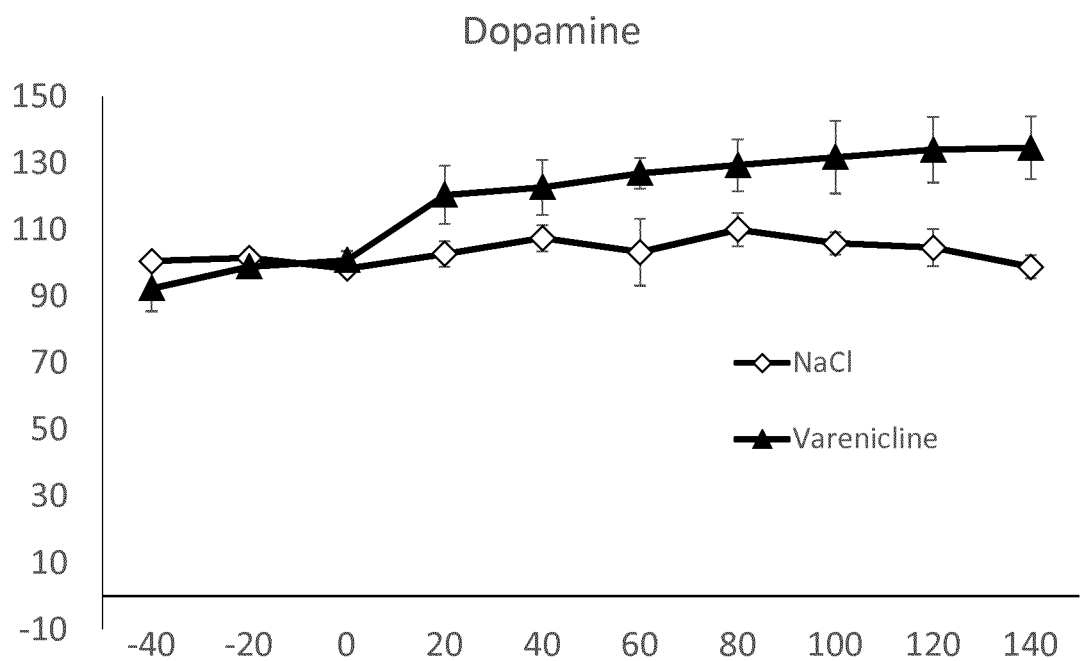
Figure 4:
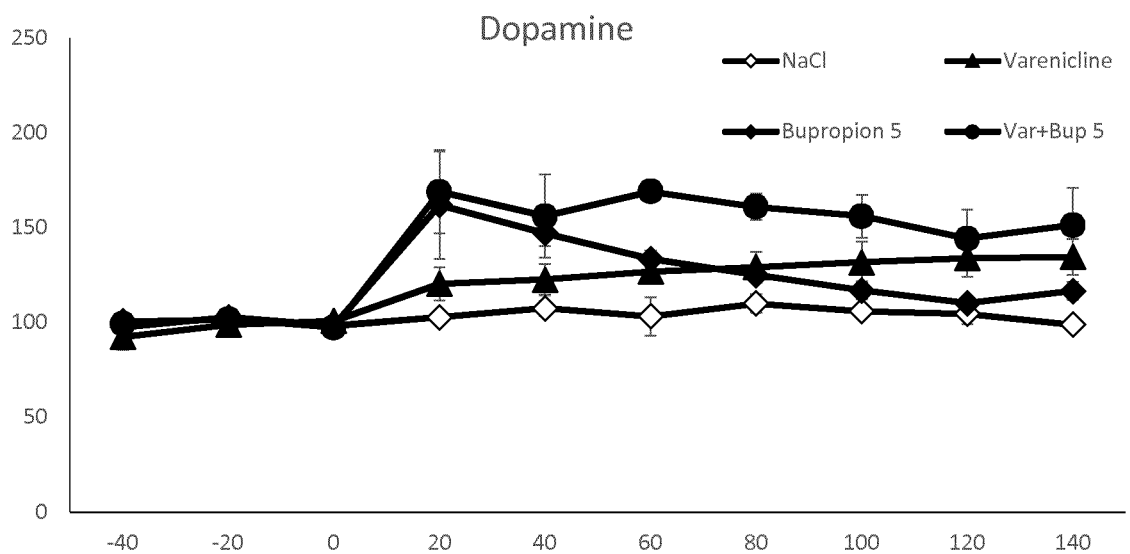
FIGS. 4 and 5 show additive effects of varenicline 1.5 mg/kg and bupropion 5 mg/kg on extracellular dopamine levels (expressed as percent of baseline) in rat nucleus accumbens.
Figure 5:
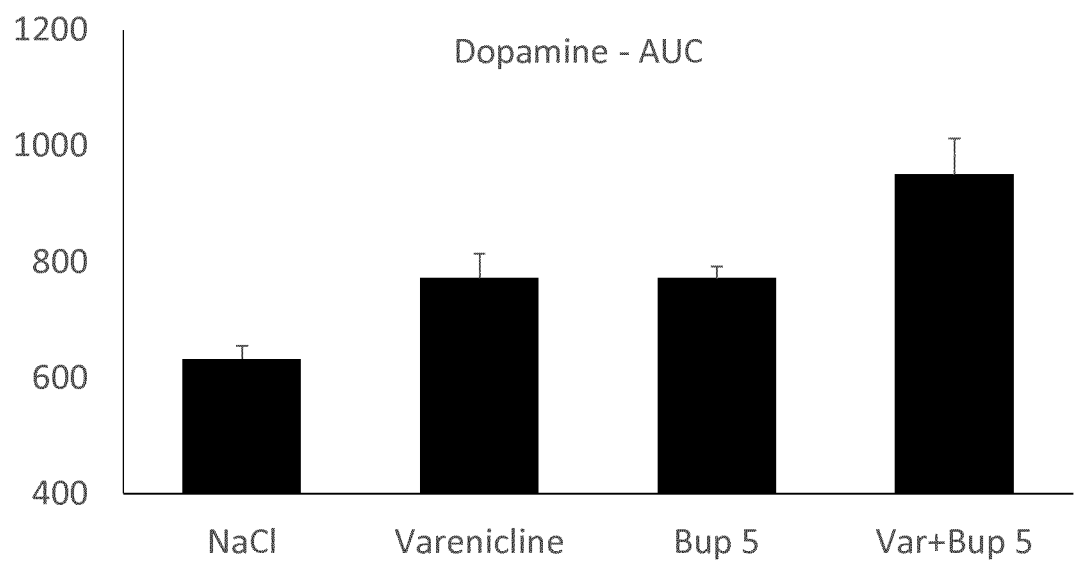

Varenicline is a smoking cessation drug that has recently been shown to possess alcohol consumption reducing properties in two randomized clinical trials (RCTs), one performed by the inventors together with the Swedish Network for Treatment Trials in the Addiction field (de Bejczy et al., 2015) and one performed in the US, in an NIAAA program for repurposing existent drugs for use in the treatment of AUD (Litten et al., 2013). The effect size was approximately 0.35 in the Swedish study and 0.4 in the American study. These data are very promising as they suggest that varenicline will outperform the previously mentioned drugs that are routinely used in the treatment of AUD.

The inventors have identified that the effect size observed for varenicline can be significantly enhanced by administering a specific combination of drugs to treat AUD and/or ARC in a subject. The inventors have concluded that by combining varenicline and bupropion an effect size of approximately 0.6-0.7 may be reached. Advantageously, treatments with effect sizes in this range are perceived as good and reliable, as exemplified by e.g. methylphenidate for adult ADHD (Castells et al., 2011) and antidepressants for depression (Hieronymus, Nilsson, & Eriksson, 2016). The availability of such a treatment has the potential to make a real difference in the care of alcohol dependent patients and in individuals with high risk drinking.

The inventors have therefore identified a novel treatment option for AUD and/or ARC using a combination of well-tolerated drugs that are already available on the market, wherein the novel treatment option achieves an effect size that is significantly enhanced compared to the drugs currently on the market for treating AUD.

The invention is based on the following principles that are brought together for the first time by the inventors to indicate that a combination of varenicline and bupropion will provide a more effective treatment option for the treatment of AUD and/or ARC.

Pioneering studies by the inventors and their colleagues revealed that, similarly to nicotine, the rewarding and reinforcing effects of ethanol are mediated via interference with brain nicotinic acetylcholine receptors (nAChRs) in the midbrain, resulting in increased neuronal firing of mesolimbic dopamine (DA) neurons and eventually dopamine release in the nucleus accumbens (nAc; ventral striatum) (for reviews, see (Soderpalm & Ericson, 2013; Soderpalm, Ericson, Olausson, Blomqvist, & Engel, 2000). The specific subtypes of nAChRs involved may differ between nicotine and ethanol, at least in the rat (Ericson, Molander, Lof, Engel, & Soderpalm, 2003), whereas the situation in man is unknown. The mechanism of action of these very often co-abused substances is thus similar but not identical, and, indeed, AUD and nicotine dependence have common underlying heredity (True et al., 1999). This background sparked animal studies (Steensland, Simms, Holgate, Richards, & Bartlett, 2007), human experimental studies (McKee et al., 2009) and so far two randomized clinical trials (RCTs) on the concept of using the anti-smoking agent varenicline for AUD. Varenicline is a partial nAChR agonist which by itself slightly raises dopamine levels in nAc but simultaneously prevents further dopamine activation by nicotine. Varenicline is the best treatment available for smoking cessation and has now also been proven effective for reducing alcohol intake in subjects with AUD, regardless of whether the afflicted subject is a nicotine user or not. In view of this, and the similarity in the interactions that ethanol and nicotine have with the rewarding mesolimbic dopamine system, the inventors have concluded that another established smoking cessation treatment, i.e. the dopamine/noradrenaline (NA) reuptake inhibitor bupropion, will be beneficial for AUD and/or ARC, and, further, that the combination of these two drugs targeting different aspects of dopamine neurotransmission will be even more effective (see below).

The status of the dopamine system in subjects with AUD is another reason that the inventors have concluded that bupropion will also work for AUD and/or ARC and that a combined treatment with varenicline and bupropion will outperform treatment with either drug alone. Both animal and human research indicate that both pre- and postsynaptic aspects of basal dopamine neurotransmission are reduced in AUD (Diana, Pistis, Carboni, Gessa, & Rossetti, 1993; Martinez et al., 2005). Furthermore, reduced dopamine neurotransmission has been associated with increased drug intake and increased relapse to drug use, in animal and human studies, respectively (Ahmed & Koob, 2005; Wang et al., 2012). In other words, the compromised dopamine system in AUD, which may be genetically determined and/or develop as an adaptation to chronic alcohol, may drive alcohol intake. Hence, alcohol intake may be reduced by increasing dopamine levels. The inventors consider the recent RCTs with varenicline to support this. When the varenicline study was launched they believed that the drug would work by a dual action, 1) by slightly stimulating dopamine neurons and thereby elevating extracellular dopamine levels, and 2) by blocking ethanol-induced activation of the dopamine neurons by occupying nAChRs that ethanol otherwise would have engaged. However, recent animal work indicates that the second mechanism may not be in play (Feduccia, Simms, Mill, Yi, & Bartlett, 2014), which in turn may be due to varenicline's failure to sufficiently interact with the specific subtypes of nAChRs that are engaged by ethanol. In that case, the effects of varenicline on AUD now observed in the two RCTs discussed above appear to derive solely from the dopamine elevating effect and as such represent proof-of-principle that elevating extracellular dopamine levels reduces alcohol intake. Further support comes from a study where the opposite was tried, i.e. chronic intramuscular administration of fluphentixole, a neuroleptic blocking postsynaptic dopamine D2 receptors. This treatment worsened the condition by producing earlier and heavier relapses to drinking, as compared to placebo (Wiesbeck et al., 2001).

The combined use of varenicline and bupropion has already been investigated for smoking cessation with results showing that the combined treatment is superior (Ebbert et al., 2014; Hall, Slade, Wells, Rose, & Levin, 2015; Rose & Behm, 2014; Vogeler, McClain, & Evoy, 2016). Given the similarities between nicotine and ethanol as outlined above and their personal insight of the medication available, its mechanism of action, and its interaction with the complex signalling pathways involved in the reward pathway, the inventors conclude that a similar superiority of the combination in the treatment of AUD and/or ARC will be observed. This particular combination is also attractive for other reasons. Bupropion is a dopamine/noradrenaline reuptake inhibitor and will hence raise also extracellular noradrenaline levels in the brain, including the frontal cortex. The inventors and others have found that drugs raising endogenous noradrenaline levels may reduce alcohol consumption (de Bejczy et al., 2015; Wilens et al., 2008) and that e.g. activation of postsynaptic alpha2-receptors in the frontal cortex may control impulsivity and thereby reduce alcohol intake (Fredriksson et al., 2015). Furthermore, when applying substances that block dopamine and noradrenaline reuptake the end effect at the neuronal terminals will be partly counteracted by activation of autoreceptors reducing both DA and NA neuronal firing (Kandel). Varenicline, via activation of nAChRs on dopamine neurons, will instead increase firing and hence counteract the effect mediated by autoreceptors, which in turn will increase the net output at the neuronal terminals. The combination of varenicline and bupropion will therefore be additive or more on dopamine output which, given the status of the dopamine system in subjects with AUD (see above), should result in a larger effect size than when giving either substance alone. Indeed, results by the inventors demonstrate this additive effect on dopamine output in the brain reward system in the rat after systemic co-administration of varenicline and bupropion (FIG. 1). Further, both drugs have been found safe to use with very limited reports of development of addiction to either of them, despite their interaction with dopamine mechanisms. A major reason for this may be their slow onsets of action. A rapid onset of action is required in order to obtain euphoric effects of dopamine activating drugs (Volkow & Swanson, 2003).

Finally, there is some evidence to support that, in humans at least, varenicline also blocks nAChRs of relevance for alcohol effects and that this contributes to the effects observed in the RCTs on AUD. McKee et al. (2009) have demonstrated that varenicline blocked ethanol-induced stimulation and euphoria in an experimental study in man. In this particular case, both mechanisms of action, i.e. blockade of ethanol-induced dopamine activation and elevation of basal dopamine levels, could be involved in the anti-drinking effect of varenicline and the addition of bupropion would boost the DA enhancing part of the combined effect, providing an improved combination treatment option for AUD and/or ARC.

The inventors have now shown, in FIGS. 1 to 5, that both the DA/NA reuptake inhibitor bupropion and the partial nAChR agonist varenicline increase extracellular DA levels in the rat nAc. Further, after combined administration an additive effect on extracellular DA levels was evident. This is most likely explained by varenicline increasing DA neuronal activity and DA release by interacting with α4β2 nAChRs possibly located both on neuronal cell-bodies in the VTA and on DA neuronal terminals in the nAc, simultaneously with bupropion preventing the released DA from reuptake at DA terminals.

Figure 6:
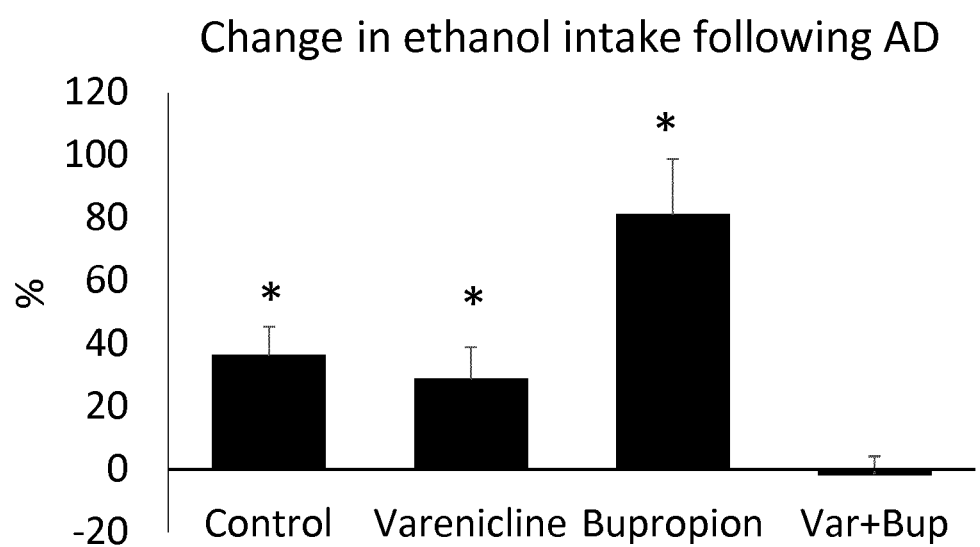
FIG. 6 shows the alcohol deprivation effect (ADE) in the Wistar rat—ethanol intake during 8 hours after reintroduction of the ethanol bottle following ethanol deprivation for two weeks. Rats were exposed to a free choice between ethanol (12% v/v) and water for 7 weeks before the ethanol deprivation period. Ethanol intake before the alcohol deprivation (AD) period is compared to that after reintroduction of ethanol in each treatment group. There was a clear ADE in all groups except in the group receiving the combined administration of varenicline 1.5 mg/kg and bupropion 5 mg/kg in which the ADE was abolished.

Interestingly, the combined administration of varenicline and bupropion completely blocked the ADE (FIG. 6). This measure is considered highly predictive for clinical effect (Spanagel and Hölter, 2000) and thus the present results suggest that the combination of varenicline and bupropion may reduce alcohol intake in man.

Signs of reduced DA neurotransmission have been associated with increased alcohol intake and increased craving and ethanol-cue reactivity, in animal (Weiss et al., 1996; Feltmann et al., 2016) and human studies (Heinz et al., 2004). Further, human research indicates that both pre- and postsynaptic components of basal DA neurotransmission are reduced in AUD (Heinz et al., 2005; Volkow et al., 2007). In other words, a compromised DA system, which may be genetically determined and/or develop as an adaptation to chronic alcohol (Volkow et al., 2006), may drive alcohol intake. Hence, it may be suggested that agents increasing DA levels might reduce alcohol intake. The recent RCTs with varenicline support this idea. When the varenicline studies were launched it was believed that the drug would work by a dual action, 1) by slightly stimulating DA neurons and thereby elevating extracellular DA levels, and 2) by blocking ethanol-induced activation of the DA neurons by occupying nAChRs that ethanol otherwise would have engaged. However, recent animal work indicates that the second mechanism may not be involved (Feduccia et al., 2014), which in turn may be due to varenicline's failure to sufficiently interact with the specific subtypes of nAChRs that are engaged by ethanol and ethanol-related cues (Ericson et al., 2003, Larsson et al., 2002, 2004; Löf et al., 2007). In that case, the effects of varenicline on AUD now observed in three RCTs may solely derive from the DA elevating effect, thereby providing proof-of-principle for that elevating extracellular DA levels reduces alcohol intake. Further support for this contention comes from a study where the opposite was tried, i.e. chronic i.m. administration of flupentixole, a neuroleptic blocking postsynaptic DA D2 receptors. This treatment worsened the condition by producing earlier and heavier relapses to drinking, as compared to placebo (Wiesbeck et al., 2001).

As pointed out above, varenicline has recently been demonstrated to reduce alcohol consumption in alcohol dependent individuals, whereas bupropion has never been tried for this indication. However, both drugs are established smoking cessation agents, with varenicline being slightly better than bupropion, and the combined use of varenicline and bupropion has been investigated for smoking cessation with results showing that the combined treatment is superior (Ebbert et al., 2014; Rose and Behm, 2014; Vogeler et al., 2016).

The varenicline+bupropion combination is attractive for the treatment of AUD/ARC for a number of reasons. Being a DA/NA reuptake inhibitor bupropion will raise also extracellular NA levels in the brain. The inventors and other researchers have found that drugs raising endogenous NA levels may reduce alcohol consumption in man (Wilens et al., 2008; deBejczy and Söderpalm, 2015). Further, when applying substances that block DA and NA reuptake the end effect at the neuronal terminals will be partly counteracted by activation of somatodendritic autoreceptors reducing both DA and NA neuronal firing (Einhorn et al., 1988). Varenicline, via activation of α4β2 nAChRs on both these types of neurons, will instead increase firing and hence counteract the effect mediated by autoreceptors, which in turn will increase the net output at the neuronal terminals (Coe et al., 2005). This action may well explain the additive effect on DA output here observed, but could apply also to the NA system. Further, both drugs have been found effective and safe across various populations and are recommended also in patients with psychiatric or addictive comorbidity (Aubin et al., 2011), despite their interaction with DA mechanisms. One reason for this may be their slow onsets of action, since a rapid onset of action is required to obtain euphoric effects of DA activating drugs (Volkow and Swanson, 2003).

Nicotine use, mainly in the form of smoking, is considerably more common among individuals with AUDs (Bien and Burge, 1990), and the severity of nicotine dependence is associated with higher craving in alcohol dependent patients (Hillemacher et al., 2006). This co-abuse imposes severe health problems and it has been claimed that alcohol dependent people more often die from smoking- than alcohol-related diseases. There is animal evidence indicating that nicotine administration as such by a pharmacological action increases alcohol intake (Potthoff et al., 1983; Blomqvist et al., 1996; Smith et al., 1999). Therefore treatment effects on nicotine intake could potentially reduce also alcohol consumption (see Prochaska et al., 2004). Also for this reason it is of considerable interest to explore the impact of smoking cessation treatments on alcohol consumption in individuals with AUD, as well as whether the tentative effect is related or unrelated to the reduction of nicotine intake.

In conclusion, the combined administration of varenicline and bupropion produced additive effects on DA release in the nAc and abolished the ADE in the rat. These findings indicate that the combination of these two drugs may outperform the effect of either drug alone in the treatment of AUD, just as is the case when using these same drugs for smoking cessation (Ebbert et al., 2014, Rose and Behm, 2014; Vogeler et al., 2016). Controlled clinical trials exploring this hypothesis in humans afflicted with AUD is highly warranted. Such trials could provide patients and practitioners with a treatment alternative with a considerably larger effect size than those presently available.

Definitions

In order that the present invention may be more readily understood, certain terms and phrases are herein defined.

As used herein, "varenicline" includes the originator drug substance (as commercially available under the name Chantix or Champix, usually in the form of varenicline tartrate) and modified derivatives thereof. Varenicline and its effective use in smoking cessation is well known. It is available on prescription and acts as a nicotinic receptor partial agonist and therefore reduces cravings for and decreases the pleasurable effects of cigarettes and other tobacco products. In this respect it is distinct in its mechanism of action from nicotinic antagonists such as e.g. bupropion (see below).

As used herein, "bupropion" includes the originator drug substance (as commercially available under the name Wellbutrin, Elontril or Zyban) and modified derivatives thereof. Bupropion and its effective use as an antidepressant and smoking cessation aid is well known. It is available on prescription and affects several different biological targets, often being described as a norepinephrine-dopamine reuptake inhibitor and a nicotinic antagonist.

As used herein, the terms "disease" and "disorder" are used interchangeably.

As used herein, "alcohol use disorder" or "AUD" refers to problem drinking that becomes severe. To be diagnosed with an AUD, individuals must meet certain criteria outlined in the Diagnostic and Statistical Manual of Mental Disorders (DSM). Under DSM-5, the current version of the DSM, anyone meeting any two of the 11 criteria during the same 12-month period receives a diagnosis of AUD. The severity of an AUD—mild, moderate, or severe—is based on the number of criteria met. Under DSM-5, individuals that answer yes to two or more of the following questions are identified as having AUD:

In the past year, have you:

Had times when you ended up drinking more, or longer than you intended?

More than once wanted to cut down or stop drinking, or tried to, but couldn't?

Spent a lot of time drinking? Or being sick or getting over the aftereffects?

Experienced craving—a strong need, or urge, to drink?

Found that drinking—or being sick from drinking—often interfered with taking care of your home or family? Or caused job troubles? Or school problems?

Continued to drink even though it was causing trouble with your family or friends?

Given up or cut back on activities that were important or interesting to you, or gave you pleasure, in order to drink?

More than once gotten into situations while or after drinking that increased your chances of getting hurt (such as driving, swimming, using machinery, walking in a dangerous area, or having unsafe sex)?

Continued to drink even though it was making you feel depressed or anxious or adding to another health problem? Or after having had a memory blackout?

Had to drink much more than you once did to get the effect you want? Or found that your usual number of drinks had much less effect than before?

Found that when the effects of alcohol were wearing off, you had withdrawal symptoms, such as trouble sleeping, shakiness, irritability, anxiety, depression, restlessness, nausea, or sweating? Or sensed things that were not there?

The invention may be used to treat alcohol risk consumption in a subject in need thereof. As used herein, and in accordance with the definition provided by NIAAA (https://www.niaaa.nih.gov/alcohol-health/overview-alcohol-consumption/moderate-binge-drinking), "alcohol risk consumption" encompasses the following: (1) above moderate drinking; (2) exhibiting a pattern of binge drinking; and (3) heavy alcohol use. As used herein, "alcohol risk consumption" therefore refers to at least one of (1) to (3).

According to the "Dietary Guidelines for Americans 2015-2020," (U.S. Department of Health and Human Services and U.S. Department of Agriculture), moderate drinking is up to 1 drink per day for women and up to 2 drinks per day for men. Accordingly, as used herein, "above moderate drinking" refers to alcohol consumption that is more than 1 drink per day for women and 2 drinks per day for men.

According to the NIAAA, "binge drinking" is a pattern of drinking that brings blood alcohol concentration (BAC) levels to 0.08 g/dL. This typically occurs after 4 drinks for women and 5 drinks for men—in about 2 hours. Furthermore, the Substance Abuse and Mental Health Services Administration (SAMHSA), which conducts the annual National Survey on Drug Use and Health (NSDUH), defines binge drinking as 5 or more alcoholic drinks for males or 4 or more alcoholic drinks for females on the same occasion (i.e., at the same time or within 2 hours of each other) on at least 1 day in the past month. Accordingly, as used herein, "exhibiting a pattern of binge drinking" refers to a subject that is consuming alcohol in a manner than brings their blood alcohol concentration to 0.08 g/dL on at least one day in the past month.

SAMHSA also defines heavy alcohol use as binge drinking on 5 or more days in the past month. Accordingly, as used herein "heavy alcohol use" refers to a subject that has exhibited a pattern of binge drinking (as defined above) on 5 or more days in the past month.

Any aspect of the invention described herein in the context of "AUD" applies equally to alcohol risk consumption (ARC).

As used here in the term "subject" refers to an individual, e.g., a human, having or at risk of having (i.e. susceptible to developing) AUD and/or ARC. The subject may be a patient i.e. a subject in need of treatment in accordance with the invention. The subject may have received treatment for the disorder or symptom. Alternatively, the subject has not been treated prior to treatment in accordance with the present invention.

As used herein, the terms "treat", "treating" and "treatment" are taken to include an intervention performed with the intention of preventing the development or altering the pathology of a disorder or symptom. Accordingly, "treatment" refers to both therapeutic treatment and prophylactic or preventative measures, wherein the object is to prevent or slow down (lessen) the targeted disorder or symptom. Accordingly, the term "treating" encompasses treating and/or preventing the development of a disorder or symptom. The invention may therefore be useful for preventing AUD and/or alcohol risk consumption in a subject that is susceptible to developing an alcohol use disorder (or indeed relapsing in AUD), and/or that is susceptible to alcohol risk consumption (or indeed relapsing into alcohol risk consumption). Accordingly, the invention may be a preventative treatment of relapse in AUD and/or alcohol risk consumption.

A subject may be treated according to the invention, by administering a combination of an effective amount of varenicline and an effective amount of bupropion (wherein the varenicline and bupropion are either in separate/distinct compositions or are combined in the same composition).

A subject may also be treated according to the invention, by administering an effective amount of varenicline to the subject, wherein the subject is (already) undergoing treatment with an effective amount of bupropion.

Similarly, a subject may also be treated according to the invention, by administering an effective amount of bupropion to the subject, wherein the subject is (already) undergoing treatment with an effective amount of varenicline.

As used herein, a subject that is "undergoing treatment" with a specified drug (e.g. varenicline or bupropion) means that the subject has already commenced treatment with the specified drug (the subject may be in any phase of the treatment e.g. induction phase, maintenance phase, recovery phase etc).

Suitably, the subject may benefit from the combination of varenicline and bupropion in accordance with the invention, in addition to other appropriate therapies for treating AUD and/or ARC, including but not limited to KBT, psychosocial therapy, brief intervention, and pharmacotherapies as naltrexone, acamprosate and disulfiram.

Suitably, the invention may be used to treat subjects with concomitant alcohol and nicotine dependence, wherein both dependencies can be treated simultaneously.

The compounds (i.e. varenicline and/or bupropion), combinations and/or compositions described herein are for administration in an effective amount. An "effective amount" (or "therapeutically effective amount") is an amount that alone, or together with further doses, produces the desired (therapeutic) response. The (therapeutically) effective amount to be used will depend, for example, upon the therapeutic objectives, the route of administration, and the condition of the subject. A suitable dosage of varenicline and/or bupropion for a given subject can be determined by an attending physician, taking into consideration various factors known to modify the action of drugs including severity and type of disease, body weight, sex, diet, time and route of administration, other medications and other relevant clinical factors. Accordingly, in one example, a suitable dose of varenicline and/or bupropion is selected based on the body weight of the subject. The dosages and schedules may be varied according to the particular disease state and the overall condition of the patient. For example, it may be necessary or desirable to reduce the above-mentioned doses of the components of the combination treatment in order to reduce toxicity. Suitable doses may also be determined based on the alcohol consumption levels of the subject (e.g. as measured by PEth concentrations in the blood). Suitable doses may also be determined for subgroups of subjects, e.g. based on their heredity and/or pharmacogenetic profile(s).

Therapeutically effective dosages may be determined by either in vitro or in vivo methods.

In one embodiment, the effective amount of varenicline may be in the range of from about 0.1 mg/day to about 5 mg/day, optionally wherein the effective amount of varenicline is in the range of from about 0.5 mg/day to about 2 mg/day. The effective amount may differ depending on the stage of treatment. For example for methods of treatment that include a variable dose regimen (see below), different doses may be effective during the induction phase(s) and the treatment (or maintenance) phase. By way of example, a first induction phase may use an initial dose of varenicline of about 0.5 mg/day. Accordingly, about 0.5 mg/day may be considered an effective amount of varenicline for use during the first induction phase. Subsequently, a second induction phase may use an increased dose of varenicline of about 1 mg/day. Accordingly, about 1 mg/day may be considered an effective amount of varenicline for use during the second induction phase. Finally, a maintenance/treatment phase may use a dose of varenicline of about 2 mg/day. Accordingly, about 2 mg/day may be considered an effective amount of varenicline for use during the treatment phase.

Similarly, the effective amount of bupropion may be in the range of from about 25 mg/day to about 600 mg/day, optionally the effective amount of bupropion may be in the range of from about 150 mg/day to about 300 mg/day. The effective amount may differ depending on the stage of treatment. For example, for methods of treatment that include a variable dose regimen (see below), different doses may be effective during the induction phase(s) and the treatment (or maintenance) phase. By way of example, a (first) induction phase may use an initial dose of bupropion of about 150 mg/day. Accordingly, about 150 mg/day may be considered an effective amount of bupropion for use during the (first) induction phase. Subsequently, a maintenance/treatment phase may use a dose of bupropion of about 300 mg/day. Accordingly, about 300 mg/day may be considered an effective amount of bupropion for use during the treatment phase.

The compounds, combinations and/or compositions described herein are therefore administered to a subject in an effective amount to produce the desired response. Examples of such responses include, but are not limited to, a reduction of alcohol consumption to lower risk levels, a reduction in the severity of AUD (as diagnosed by the 11 criteria set out above), and increase in survival rate. Methods for measuring the response to treatment are well known, and include for example measuring alcohol intake of the subject. Suitable methods for measuring alcohol intake are well known in the art, and include measuring phosphatidylethanol (PEth) and/or other alcohol markers in a blood sample of the subject (Hashimoto et al., 2013; Walther et al., 2015), performing an Alcohol timeline followback (TLFB) (Sobell & Sobell, 1992) assessment on the subject, AUDIT questionnaire (Saunders, Aasland, Amundsen, & Grant, 1993), assessing the subject's craving for alcohol, and/or determining the individual's obsessive compulsive drinking score (OCDS) (Anton, Moak, & Latham, 1995).

Preferably, the combination(s) and/or composition(s) described herein will provide a beneficial or synergistic effect on the treatment of AUD and/or ARC in a subject in need thereof. A combination treatment is defined as affording a "synergistic effect" or a "synergistic treatment" if the effect is therapeutically superior, as measured by, for example, the extent of the response, the response rate, the time to disease progression or the survival period, to that achievable on dosing one or other of the components of the combination treatment at its conventional dose. For example, the effect of the combination treatment is synergistic if the effect is therapeutically superior to the effect achievable with varenicline alone or bupropion alone. Further, the effect of the combination is synergistic if a beneficial effect is obtained in a group of subjects that does not respond (or responds poorly) to varenicline or bupropion alone. In addition, the effect of the combination treatment is defined as affording a synergistic effect if one of the components is dosed at its conventional dose and the other component is dosed at a reduced dose and the therapeutic effect, as measured by, for example, the extent of the response, the response rate, the time to disease progression or the survival period, is equivalent to or better than that achievable on dosing conventional amounts of either one of the components of the combination treatment. In particular, synergy is deemed to be present if the conventional dose of varenicline or bupropion may be reduced without detriment to one or more of the extent of the response, the response rate, the time to disease progression and survival data, in particular without detriment to the duration of the response, but with fewer and/or less troublesome side-effects than those that occur when conventional doses of each component are used.

Accordingly, the effective amount of varenicline may be lower when used in combination with bupropion than the examples given above of about 0.5 mg/day for the first induction dose, about 1 mg/day for the second induction dose and about 2 mg/day for the maintenance dose. Accordingly, the effective dose may be less than or equal to about 2 mg/day for a maintenance dose (e.g. less than or equal to 2 mg/day, less than or equal to 1.8 mg/day, less than or equal to 1.6 mg/day, less than or equal to 1.4 mg/day, less than or equal to 1.2 mg/day, less than or equal to 1 mg/day), less than or equal to about 1 mg/day for a second induction dose (e.g. less than or equal to 1 mg/day, less than or equal to 0.9 mg/day, less than or equal to 0.8 mg/day, less than or equal to 0.7 mg/day, less than or equal to 0.6 mg/day, less than or equal to 0.5 mg/day), and less than or equal to about 0.5 mg/day for a first induction dose (e.g. less than or equal to 0.5 mg/day, less than or equal to 0.4 mg/day, less than or equal to 0.3 mg/day, less than or equal to 0.2 mg/day, less than or equal to less than 0.1 mg/day).

Similarly, the effective amount of bupropion may be lower when used in combination with varenicline than the examples given above of about 150 mg/day for the (first) induction dose, and about 300 mg/day for the maintenance dose. Accordingly, the effective dose may be less than or equal to about 300 mg/day for a maintenance dose (e.g. less than or equal to 300 mg/day, less than or equal to 250 mg/day, less than or equal to 200 mg/day, less than or equal to 150 mg/day), and less than or equal to about 150 mg/day for a (first) induction dose (e.g. less than or equal to 150 mg/day, less than or equal to 125 mg/day, less than or equal to 100 mg/day, less than or equal to 75 mg/day, less than or equal to 50 mg/day, less than or equal to 25 mg/day).

As used herein, a "combination" comprising varenicline and bupropion encompasses a dosage form of varenicline for use in combination with a distinct dosage form of bupropion, as well as a dosage form comprising both varenicline and bupropion. "Combined use" and "combination" in the context of the invention therefore also includes a product comprising both varenicline and bupropion, as discrete separate dosage forms, in separate containers or e.g. in blisters containing both types of drugs in discrete solid dosage units, e.g. in a form in which the dosage units which have to be taken together or which have to be taken within one day are grouped together in a manner which is convenient for the subject. Said product itself or as a part of a kit may contain instructions for the simultaneous, sequential or separate administration of the discrete separate dosage units, to a subject. Accordingly, the product may comprise at least two compounds (e.g. varenicline and bupropion) as discrete separate dosage forms, in a form which is suitable for sequential, separate and/or simultaneous administration.

The compounds, combinations and/or compositions may be provided in a form which is suitable for sequential (consecutive), separate and/or simultaneous (concurrent) administration to the subject, in any order. For example, varenicline may be provided in a form that is suitable for sequential, separate and/or simultaneous administration to bupropion. Accordingly, varenicline may be administered to the subject at the same time or at a different time (before or after) compared to when bupropion is administered. In cases where varenicline and bupropion are administered simultaneously, the varenicline and bupropion may be administered as separate compositions that are administered at the same time, or may be administered as a combined composition that includes both varenicline and bupropion.

The compounds, combinations and/or compositions described herein can be administered to the subject by any conventional route, including oral administration (for example in tablet form), injection or by gradual infusion over time. The administration may, for example, be topical, oral, parenteral, intravenous, intraperitoneal, intramuscular, intravascular, intracavity, intranasal, intracerebral, intratracheal, intralesional, intraperitoneal, rectal, subcutaneous, transdermal, epidural, percutaneous, or by infusion. By way of example, varenicline can be administered orally (e.g. in tablet form or as a chewing gum composition—see EP1863442), transdermally (see EP1909773), via controlled release (see WO2009034431), or may be formulated for intranasal, buccal, sublingual and pulmonary delivery (see EP1802276). Several suitable means for administering bupropion are also well known (see for example EP1575565 (oral administration using tablet form); and WO2007117581 (transdermal administration)). In one example, varenicline and bupropion are provided in distinct compositions that are suitable for e.g. sublingual administration, administration by nasal spray, implantation, and or administration by pump.

The compounds, combinations and/or compositions described herein may therefore be in a form suitable for the above modes of administration. For example, suitable forms for oral administration include a tablet or capsule; suitable forms for nasal administration or administration by inhalation include a powder or solution; suitable forms for parenteral injection (including intravenous, subcutaneous, intramuscular, intravascular or infusion) include a sterile solution, suspension or emulsion; suitable forms for topical administration include a patch, an ointment or cream; and suitable forms for rectal administration include a suppository. Alternatively, the route of administration may be by injection.

The compositions of the present invention are advantageously presented in unit dosage form. Dosage forms (also called unit doses) are pharmaceutical drug products in the form in which they are marketed for use, with a specific mixture of active ingredients and inactive components (excipients), in a particular configuration (such as a capsule shell, for example), and apportioned into a particular dose. Depending on the route of administration, dosage forms include liquid, solid, and semisolid dosage forms. Common dosage forms include pills, tablet, capsule, drinks or syrups.

In one example, the combination of varenicline and bupropion is provided in the form of a depot preparation, wherein varenicline and bupropion have be formulated to have the same or different release rates. As used herein, a "depot preparation" refers to a specific formulation of the varenicline and bupropion compounds that is given by injection, wherein the medication is slowly released into the body of the subject over a number of days or weeks.

In one example, an effective dose of varenicline may be combined with the corresponding effective dose of bupropion in a unit dosage form (e.g. a tablet) for daily oral administration by the subject.

Where the administration of the separate formulations of varenicline and bupropion is sequential or separate, the delay in administering the second formulation should not be such as to lose the beneficial effect of the combination therapy.

Varenicline and/or bupropion may be part of a composition (e.g. a pharmaceutical composition) that comprises the compound (i.e. varenicline and/or bupropion) and one or more other components. A composition may be a pharmaceutical composition that comprises varenicline and/or bupropion and a pharmaceutically acceptable excipient, adjuvant, diluent and/or carrier. Pharmaceutical compositions may routinely contain pharmaceutically acceptable concentrations of salt, buffering agents, preservatives, compatible carriers, supplementary immune potentiating agents such as adjuvants and cytokines and optionally other therapeutic agents or compounds.

As used herein, "pharmaceutically acceptable" refers to a material that is not biologically or otherwise undesirable, i.e., the material may be administered to an individual along with the selected compound without causing any undesirable biological effects or interacting in a deleterious manner with any of the other components of the pharmaceutical composition in which it is contained.

Excipients are natural or synthetic substances formulated alongside an active ingredient (e.g. a compound of the invention), included for the purpose of bulking-up the formulation or to confer a therapeutic enhancement on the active ingredient in the final dosage form, such as facilitating drug absorption or solubility. Excipients can also be useful in the manufacturing process, to aid in the handling of the active substance concerned such as by facilitating powder flowability or non-stick properties, in addition to aiding in vitro stability such as prevention of denaturation over the expected shelf life. Pharmaceutically acceptable excipients are well known in the art. A suitable excipient is therefore easily identifiable by one of ordinary skill in the art. By way of example, suitable pharmaceutically acceptable excipients include water, saline, aqueous dextrose, glycerol, ethanol, and the like.

Adjuvants are pharmacological and/or immunological agents that modify the effect of other agents in a formulation. Pharmaceutically acceptable adjuvants are well known in the art. A suitable adjuvant is therefore easily identifiable by one of ordinary skill in the art.

Diluents are diluting agents. Pharmaceutically acceptable diluents are well known in the art. A suitable diluent is therefore easily identifiable by one of ordinary skill in the art.

Carriers are non-toxic to recipients at the dosages and concentrations employed and are compatible with other ingredients of the formulation. The term "carrier" denotes an organic or inorganic ingredient, natural or synthetic, with which the active ingredient is combined to facilitate the application. Pharmaceutically acceptable carriers are well known in the art. A suitable carrier is therefore easily identifiable by one of ordinary skill in the art.

The compounds, compositions and/or combinations of the invention may be administered using any suitable method and dosage form, as described in detail above.

By way of example, varenicline may be administered to a subject in need thereof using a variable dose method for treating AUD and/or ARC, wherein the method comprises at least one induction dose, with a subsequent treatment dose (also known as a maintenance dose). Appropriate variable dose methods for administration of varenicline to humans are well known. As one example, varenicline may be administered in the following doses: first induction dose (days 1 to 3) of 0.5 mg/day; second induction dose (days 4 to 7) of 1 mg/day (e.g. in 2×0.5 mg dosage forms); maintenance dose (from day 8 to 98) of 2 mg/day (e.g. in 4×0.5 mg dosage forms). This example treatment regimen is for a total of 14 weeks, including 12 weeks of steady state treatment.

The daily induction and/or maintenance dose of varenicline may be administered as a single dose, or as a series of doses (wherein the series of doses are to be taken simultaneously, or are taken sequentially e.g. spread out during the day). For example, if the daily second induction dose of varenicline is 1 mg/day, this can either be administered as 1 mg once a day (e.g. two tablets of 0.5 mg, taken simultaneously) or as 0.5 mg twice a day (e.g. one tablet of 0.5 mg in the morning and one tablet of 0.5 mg in the evening).

Although a specific variable dose regimen for varenicline is provided above, the invention is not limited to this variable dose regimen; the specific dosages, number of days for each dose and the concentration of each dosage form may vary depending on several factors such as severity of AUD and/or ARC, sex, weight, age etc of the subject. Identifying appropriate dose regimens for the administration of varenicline to treat AUD and/or ARC in subjects in need thereof is within the routine capabilities of a person of skill in the art.

By way of a further example, bupropion may be administered to a subject in need thereof using a variable dose method for treating AUD and/or ARC, wherein the method comprises at least one induction dose, with a subsequent treatment dose (also known as a maintenance dose). Appropriate variable dose methods for administration of bupropion to humans are well known. As one example, bupropion may be administered in the following doses: first induction dose (days 1 to 7) of 150 mg/day; maintenance dose (from day 8 to 98) of 300 mg/day (e.g. in 2×150 mg dosage forms). This example treatment regimen is for a total of 14 weeks, including 12 weeks of steady state treatment).

As described above in respect of varenicline, the daily induction and/or maintenance dose of bupropion may be administered as a single dose, or as a series of doses (wherein the series of doses are to be taken simultaneously, or are taken sequentially e.g. spread out during the day). For example, if the daily maintenance dose of bupropion is 300 mg/day, this can either be administered as 300 mg once a day (e.g. two tablets of 150 mg, taken simultaneously) or as 150 mg twice a day (e.g. one tablet of 150 mg in the morning and one tablet of 150 mg in the evening).

Although a specific variable dose regimen for bupropion is provided above, the invention is not limited to this regimen; the specific dosages, number of days for each dose and the concentration of each dosage form may vary depending on several factors such as severity of AUD and/or ARC, sex, weight, age etc of the subject. Identifying appropriate dose regimens for the administration of bupropion to treat AUD and/or ARC in subjects in need thereof is within the routine capabilities of a person of skill in the art.

For the avoidance of doubt, the invention is directed to the combined use of varenicline and bupropion for treating AUD and/or ARC, and thus the invention may be achieved by combining the two specific variable dose regimens for varenicline and bupropion provided above. As mentioned previously, the dosage forms for varenicline and bupropion may be suitable for separate, simultaneous or sequential administration.

Preferably, the daily dose amounts of varenicline (or bupropion) are administered to the subject as a single dose, or alternatively are administered as multiple doses. As used herein, the term "dose" refers to an amount of the drug (varenicline or bupropion) which is administered to the subject.

As used herein, the term "variable dose" includes different doses of the compound varenicline and/or bupropion) which are administered to a subject for therapeutic treatment. "Variable dose regimen" or "variable dose therapy" describe a treatment schedule that is based on administering different amounts of the compound (e.g. varenicline and/or bupropion) at various time points throughout the course of treatment. In one embodiment, the invention describes a variable dose method of treatment comprising an induction phase and a treatment phase, wherein the compound (varenicline and/or bupropion) is administered at a lower dose during the induction phase than the treatment phase. As used herein, the terms "maintenance phase" and "treatment phase" are used interchangeably. Similarly, "maintenance dose" and "treatment dose" are used interchangeably.

The term "induction phase" refers to a period of treatment comprising administering of the compound (varenicline and/or bupropion) to a subject in order to attain a threshold level. During the induction phase, at least one induction dose of the compound (varenicline and/or bupropion) is administered to a subject suffering from AUD and/or ARC.

The induction phase may vary in length (e.g. at least 1, 2, 3, 4, 5, 6, 7, days). Typically, the induction phase is 5 to 8 days (usually 7 days) in the treatment of AUD and/or ARC in accordance with the invention. The induction phase may be split into e.g. a first induction phase and a second induction phase if more than one induction dose is to be used. In this case, the first induction phase may be about 1 to 3 days, and the second induction phase may subsequently be an additional 1 to 4 days (e.g. first induction phase—day 1 to 3, second induction phase—day 4 to 7, treatment phase—day 8 onwards).

The term "threshold level" refers to therapeutically effective level of the compound (varenicline and/or bupropion) in a subject. A threshold level is achieved by administering at least one induction dose during the induction phase of treatment. Any number of induction doses may be administered to achieve a threshold level of the compound (varenicline and/or bupropion).

Once a threshold level is achieved, the treatment phase is initiated.

The term "induction dose" refers to the first dose of the compound (varenicline and/or bupropion), which is smaller in comparison to the maintenance or treatment dose. The induction dose can be a single dose or alternatively, a set of doses.

The induction dose is often used to bring the drug in the body to a steady state amount. The induction dose is administered during the induction phase of the therapy. The induction dose may be increased during the induction phase. For example, the induction phase for varenicline administration may be split into a first induction phase (wherein a first induction dose of e.g. 0.5 mg varenicline/day is administered) and a second induction phase (wherein a second induction dose of e.g. 1 mg/day is administered). Alternatively, the induction dose may remain constant during the induction phase (e.g. an induction dose of about 150 mg/day of bupropion).

The "treatment phase" or "maintenance phase" refers to a period of treatment comprising administration of a compound (varenicline and/or bupropion) to a subject in order to achieve and maintain a desired therapeutic effect. The treatment phase follows the induction phase, and therefore is initiated once a threshold level is achieved.

The term "treatment dose" or "maintenance dose" is the amount of compound (varenicline and/or bupropion) taken by a subject to achieve and maintain a desired therapeutic effect. A treatment dose is administered subsequent to the induction dose. A treatment dose can be a single dose, or alternatively, a set of doses. A treatment dose is administered during the treatment phase of the therapy. Treatment doses are higher than the induction dose and can be equal to each other when administered in succession. Typically, the maintenance dose remains constant throughout the treatment phase of the therapy (e.g. about 300 mg/day for bupropion; about 2 mg/day for varenicline), however, the maintenance dose may also be varied (e.g. reduced) during the treatment phase, provided that the desired therapeutic effect is maintained.

The treatment phase of the therapy may be of any appropriate length. By way of example, the treatment phase may be at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks. Typically, the treatment phase for AUD and/or ARC is at least 12 weeks.

In one aspect, the invention also provides a combination comprising an effective amount of varenicline and an effective amount of an additional drug with dopaminergic effect for use in treating alcohol use disorder and/or treating alcohol risk consumption in a subject in need thereof. In one aspect, the additional drug with dopaminergic effect is bupropion.

In one aspect, the invention also provides a combination comprising an effective amount of bupropion and an effective amount of an additional drug with nicotinergic effect for use in treating alcohol use disorder and/or treating alcohol risk consumption in a subject in need thereof. In one aspect, the additional drug with nicotinergic effect is varenicline.

In one aspect, the invention also provides a combination comprising an effective amount of a drug with nicotinergic effect and an effective amount of an additional drug with dopaminergic effect for use in treating alcohol use disorder and/or treating alcohol risk consumption in a subject in need thereof.

Aspects of the invention are demonstrated by the following non-limiting examples.

EXAMPLES

A large body of evidence obtained in rats and mice demonstrates that ethanol and nicotine interact with the brain reward system by similar but not identical pharmacological mechanisms (see Söderpalm et al., 2000; Söderpalm and Ericson, 2013). Thus, ethanol's activation of the mesolimbic dopamine (DA) system resulting in elevation of extracellular DA levels in the nucleus accumbens (nAc; ventral striatum) involve nicotinic acetylcholine receptors (nAChRs) in the anterior ventral tegmental area (VTA) (Blomqvist et al. 1997; Ericson et al., 2008). Further, unspecific blockade of these receptors either by systemic administration of mecamylamine or by site-directed injections in the VTA reduces ethanol intake and preference in the rat (Blomqvist et al., 1996; Ericson et al., 1998). Originally it was believed that ethanol produces these effects by direct interference with nAChRs, since ethanol indeed may interact with nAChRs (Cardoso et al., 1999), but subsequent studies showed that the involvement instead most likely is indirect and due to liberation of acetylcholine in the VTA (Ericson et al., 2003; Larsson et al., 2005). Further, the subtypes of nAChRs involved in the VTA appear to be α3, β3 or α6 containing subtypes (Larsson et al., 2004) and not the α4β2 by which nicotine activates the mesolimbic DA system (Corrigall et al., 1994; Picciotto et al., 1998; Larsson et al., 2002; Ericson et al., 2003). Interestingly, the same nAChR subtypes involved in the pharmacological action of ethanol appear to be involved also in ethanol cue-induced DA release in the nAc as well as in ethanol cue-reinforced behavior (Löf et al., 2007).

The above studies led to the hypothesis that varenicline, a partial agonist at nAChR and the most efficient smoking cessation agent available (Aubin et al., 2011) may reduce ethanol intake. This was demonstrated in several models of ethanol intake in the rat (Steensland et al., 2007) and experimental studies in high-alcohol consuming smokers demonstrated an effect of varenicline on alcohol craving, alcohol-induced "high" and alcohol intake also in man (McKee et al., 2009). These findings prompted two randomized control trials (RCTs), one American and one Swedish, which were launched almost simultaneously but independently of each other to test this hypothesis in alcohol dependent individuals. The American study (Litten et al., 2013) showed a significant reduction of alcohol intake measured by the TimeLineFollowBack Method (effect size approx. 0.4 (Cohen's d)), whereas the Swedish study (de-Bejczy et al., 2015) found significant reductions of blood levels of the specific alcohol consumption marker phosphatidylethanol (Cohen's d=0.35), as well as of AUDIT (Alcohol Use Disorder Identification Test) and OCRS (the Obsessive Compulsive Rating Scale) scores. Recently yet another RCT was published in electronic form showing an effect size of 0.45 for varenicline in male alcoholics but no effect in females (O'Malley et al., 2017). The effect sizes in these three studies thus are larger than those observed in meta-analyses of studies performed on the currently approved alcohol anti-relapse pharmacotherapies naltrexone and acamprosate (0.2-0.3) (Srisurapanont and Jarusuraisin, 2002; Soyka and Chick, 2003; Jonas et al., 2014).

Both varenicline and the DA/noradrenaline (NA) reuptake inhibitor bupropion are efficient smoking cessation agents (Aubin et al., 2011). Interestingly, combined administration of these drugs produce additive effects on smoking cessation (Ebbert et al., 2014; Rose and Behm, 2014; Vogeler et al., 2016). This additive effect is probably at least partly related to these drugs' complimentary means to enhance extracellular DA levels in the ventral striatum— varenicline by stimulating neuronal firing and DA release and bupropion by inhibiting DA reuptake. Animal studies and brain imaging studies in humans indicate that compromised DA systems after chronic exposure to drugs of abuse are related to increased drug intake and relapse, respectively (Weiss et al., 1996; Wang et al., 2012; Feltmann et al., 2016). Therefore increasing basal DA activity may reduce drug intake.

Boosting of the alcohol intake reducing effect already demonstrated for varenicline with bupropion would be a highly desirable option in the treatment of AUD tentatively producing an effect size >0.5. In the present study we therefore explored the combined action of varenicline and bupropion on DA levels in the nAc, using in vivo microdialysis in awake freely moving rats, and on the alcohol deprivation effect (ADE), an animal model with a high predictive value for the clinical outcome in man (Spanagel and Hölter, 2000).

The following examples evaluate the efficacy and safety of a treatment regimen combining varenicline and bupropion in an animal model for AUD (example 1) and human subjects with AUD (example 2).

Example 1

A). Experiments that examine the effects of varenicline and bupropion (separately and in combination) on dopamine release in the nucleus accumbens (nAc; a central part of the brain reward system) using in vivo microdialysis in awake, freely moving rats have commenced. Preliminary data indicates that the addition of bupropion boosts the increased dopamine output induced by varenicline. Rats were surgically implanted with a microdialysis probe into nAc, which two days later was coupled to a perfusion pump allowing liquid sampling from the extracellular space. After a stable baseline was obtained varenicline (1.5 mg/kg, s.c.), bupropion (2.5 mg/kg, i.p.) or control solution was administered and sampling continued for 140 minutes. As seen in FIG. 1, both varenicline and bupropion raise extracellular dopamine levels in the dialysate. Further, as long as bupropion produces an effect, this effect adds to the varenicline effect when the two drugs are given in combination. The inventors expect higher doses of bupropion to have a longer duration of action and that the additive effect on the varenicline effect will be correspondingly prolonged.

B). A two-bottle choice test (water vs. ethanol) intermittent access model will be performed in the rat. Animals with a high ethanol intake and preference (over water) will be selected. These ethanol high-preferring rats will be randomized to four treatment groups (control+control, varenicline+ control, control+bupropion, varenicline+bupropion) for subchronic treatment (14 days), using doses selected from the in vivo microdialysis experiments (A above) and that have shown additive or potentiating effect on dopamine output. The effects both on on-going drinking and on the enhanced alcohol intake observed after two weeks of abstinence (the alcohol deprivation effect, an animal model of relapse) will be determined. Both these measures are considered predictive for clinical outcome in humans.

Example 2

A randomized placebo-controlled double-blind four-armed multicenter trial will be used to evaluate the efficacy of varenicline and bupropion (separately) and the combination of varenicline and bupropion versus placebo on AUD.

Duration; 2 weeks of titration and 12 weeks of steady state period with a maintenance dose of study drug.

Arm 1: subjects are randomised to receive varenicline+ placebo,

Arm 2: subjects are randomised to receive bupropion+ placebo,

Arm 3: subjects are randomized to receive varenicline+ bupropion,

Arm 4: subjects are randomized to receive placebo+ placebo

Varenicline will be administered in the following doses; day 1-3; 0.5 mg×1, day 4-7; 0.5 mg×2, from day 8; 0.5 mg×4. Hence a daily maintenance dose of 2 mg.

Bupropion will be administered in the following doses; day 1-7; 150 mg×1, from day 8; 150 mg×2. Hence a daily maintenance dose of 300 mg.

For subjects receiving varenicline and bupropion, the combination of drugs will be administered at the same time.

Inclusion Criteria:

Age 25-75, men and women

Alcohol dependence according to DSM criteria with a minimum of 5 criteria

Current alcohol consumption, as measured by positive PEth analysis (e.g. over 0.5 which is equivalent of approx. 60 g alcohol per day) at screening and at randomization Exclusion Criteria:

Current severe somatic or psychiatric illness

Including unstable hypertensive disease (>140/90)

Gastric by-pass or other invasive obesity treatment

BMI >30

Concomitant medication possibly influencing study results

Current depression, anxiety syndrome,

Neuopsychiatric diagnose

Suicidality

Withdrawal seizures during the last five years

Delirium tremens, lifetime

SUD diagnose other than alcohol and nicotine

Current drug use

Liver enzymes (AST, ALT) values of >3 times upper limits

Primary Outcome Measures:

Specific alcohol marker Phosphatidylethanol (PEth) levels in blood

Secondary Outcome Measures:

Self-reported alcohol consumption, measured by Timeline Follow Back (TLFB) and self-report questionnaire AUDIT Alcohol craving, measured by Visual Analogue Scale (VAS)

Additional alcohol markers carbohydrate-deficient transferrin (CDT) and gamma-glutamyl transferase (GGT), measured by levels in blood Cognitive functions, measured by Cambridge Neuropsychological Test Battery (CANTAB)

Nicotine use, measured by cotinine levels in blood

Inflammatory variables measured by high sensitivity C-reactive Protein (hsCRP)

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1 94); and Hale and Marham, The Harper Collins Dictionary of Biology, Harper Perennial, NY (1991) provide those of skill in the art with a general dictionary of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a", "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent, or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

REFERENCES

Ahmed, S. H., & Koob, G. F. (2005). Transition to drug addiction: a negative reinforcement model based on an allostatic decrease in reward function. *Psychopharmacology (Berl)*, 180(3), 473-490. doi:10.1007/s00213-005-2180-z Anton, R. F., Moak, D. H., & Latham, P. (1995). The Obsessive Compulsive Drinking Scale: a self-rated instrument for the quantification of thoughts about alcohol and drinking behavior. *Alcoholism, clinical and experimental research*, 19(1), 92-99.

CAN. (2014). Drogutvecklingen i Sverige 2014. *Rapport* 144.

Castells, X., Ramos-Quiroga, J. A., Rigau, D., Bosch, R., Nogueira, M., Vidal, X., & Casas, M. (2011). Efficacy of methylphenidate for adults with attention-deficit hyperactivity disorder: a meta-regression analysis. *CNS Drugs*, 25(2), 157-169. doi:10.2165/11539440-000000000-00000 de Bejczy, A., Lof, E., Walther, L., Guterstam, J., Hammarberg, A., Asanovska, G., . . . Soderpalm, B. (2015). Varenicline for treatment of alcohol dependence: a randomized, placebo-controlled trial. *Alcohol Clin Exp Res*, 39(11), 2189-2199. doi:10.1111/acer.12854

Diana, M., Pistis, M., Carboni, S., Gessa, G. L., & Rossetti, Z. L. (1993). Profound decrement of mesolimbic dopaminergic neuronal activity during ethanol withdrawal syndrome in rats: electrophysiological and biochemical evidence. *Proc Natl Acad Sci USA*, 90(17), 7966-7969.

Diehl, A., Ulmer, L., Mutschler, J., Herre, H., Krumm, B., Croissant, B., . . . Kiefer, F. (2010). Why is disulfiram superior to acamprosate in the routine clinical setting? A retrospective long-term study in 353 alcohol-dependent patients. *Alcohol Alcohol*, 45(3), 271-277. doi:10.1093/alcalc/agq017

Donoghue, K., Elzerbi, C., Saunders, R., Whittington, C., Pilling, S., & Drummond, C. (2015). The efficacy of acamprosate and naltrexone in the treatment of alcohol dependence, Europe versus the rest of the world: a meta-analysis. *Addiction*, 110(6), 920-930. doi:10.1111/add.12875

Ebbert, J. O., Hatsukami, D. K., Croghan, I. T., Schroeder, D. R., Allen, S. S., Hays, J. T., & Hurt, R. D. (2014). Combination varenicline and bupropion SR for tobacco-dependence treatment in cigarette smokers: a randomized trial. *JAMA*, 311(2), 155-163. doi:10.1001/jama.2013.283185

Ericson, M., Molander, A., Lof, E., Engel, J. A., & Soderpalm, B. (2003). Ethanol elevates accumbal dopamine levels via indirect activation of ventral tegmental nicotinic acetylcholine receptors. *Eur J Pharmacol*, 467(1-3), 85-93.

Feduccia, A. A., Simms, J. A., Mill, D., Yi, H. Y., & Bartlett, S. E. (2014). Varenicline decreases ethanol intake and increases dopamine release via neuronal nicotinic acetylcholine receptors in the nucleus accumbens. *Br J Pharmacol*, 171(14), 3420-3431. doi:10.1111/bph.12690

Fredriksson, I., Jayaram-Lindstrom, N., Wirf M., Nylander, E., Nystrom, E., Jardemark, K., & Steensland, P. (2015). Evaluation of guanfacine as a potential medication for alcohol use disorder in long-term drinking rats: behavioral and electrophysiological findings. *Neuropsychopharmacology*, 40(5), 1130-1140. doi:10.1038/npp.2014.294

Hall, B. J., Slade, S., Wells, C., Rose, J. E., & Levin, E. D. (2015). Bupropion-varenicline interactions and nicotine self-administration behavior in rats. *Pharmacol Biochem Behav*, 130, 84-89. doi:10.1016/j.pbb.2015.01.009

Hashimoto, E., Riederer, P. F., Hesselbrock, V. M., Hesselbrock, M. N., Mann, K., Ukai, W., . . . Saito, T. (2013). Consensus paper of the WFSBP task force on biological markers: biological markers for alcoholism. *World J Biol Psychiatry,* 14(8), 549-564. doi:10.3109/15622975.2013.838302

Heather, N., Adamson, S. J., Raistrick, D., Slegg, G. P., & Team, U. R. (2010). Initial preference for drinking goal in the treatment of alcohol problems: I. Baseline differences between abstinence and non-abstinence groups. *Alcohol Alcohol,* 45(2), 128-135. doi:10.1093/alcalc/agp096

Hieronymus, F., Nilsson, S., & Eriksson, E. (2016). A mega-analysis of fixed-dose trials reveals dose-dependency and a rapid onset of action for the antidepressant effect of three selective serotonin reuptake inhibitors. *Transl Psychiatry,* 6(6), e834. doi:10.1038/tp.2016.104

Hodgins, D. C., Leigh, G., Milne, R., & Gerrish, R. (1997). Drinking goal selection in behavioral self-management treatment of chronic alcoholics. *Addict Behav,* 22(2), 247-255.

Johnson, A. (2000). Hur mycket kostar supen?: om alkohol och samhällsekonomi.

Jonas, D. E., Amick, H. R., Feltner, C., Bobashev, G., Thomas, K., Wines, R., . . . Garbutt, J. C. (2014). Pharmacotherapy for adults with alcohol use disorders in outpatient settings: a systematic review and meta-analysis. *JAMA,* 311(18), 1889-1900. doi:10.1001/jama.2014.3628

Jorgensen, C. H., Pedersen, B., & Tonnesen, H. (2011). The efficacy of disulfiram for the treatment of alcohol use disorder. *Alcoholism, clinical and experimental research,* 35(10), 1749-1758. doi:10.1111/j.1530-0277.2011.01523.x Kandel, E. R. *Principals of neuoral science.*

Kohn, R., Saxena, S., Levav, I., & Saraceno, B. (2004). The treatment gap in mental health care. *Bull World Health Organ,* 82(11), 858-866. doi:/S0042-96862004001100011

Laaksonen, E., Koski-Jannes, A., Salaspuro, M., Ahtinen, H., & Alho, H. (2008). A randomized, multicentre, open-label, comparative trial of disulfiram, naltrexone and acamprosate in the treatment of alcohol dependence. *Alcohol Alcohol,* 43(1), 53-61. doi:10.1093/alcalc/agm136

Lesch, O. M., Lesch, E., Dietzel, M., Mader, R., Musalek, M., Walter, H., & Zeiler, K. (1986). [Chronic alcoholism—alcohol sequelae—causes of death]. *Wien Med Wochenschr,* 136(19-20), 505-515.

Lido, H. H., Marston, H., Ericson, M., & Soderpalm, B. (2012). The glycine reuptake inhibitor Org24598 and acamprosate reduce ethanol intake in the rat; tolerance development to acamprosate but not to Org24598. *Addiction biology,* 17(5), 897-907. doi:10.1111/j.1369-1600.2011.00367.x Litten, R. Z., Ryan, M. L., Fertig, J. B., Falk, D. E., Johnson, B., Dunn, K. E., . . . Stout, R. (2013). A double-blind, placebo-controlled trial assessing the efficacy of varenicline tartrate for alcohol dependence. *J Addict Med,* 7(4), 277-286. doi:10.1097/ADM.0b013e31829623f4

Maisel, N. C., Blodgett, J. C., Wilbourne, P. L., Humphreys, K., & Finney, J. W. (2013). Meta-analysis of naltrexone and acamprosate for treating alcohol use disorders: when are these medications most helpful? *Addiction,* 108(2), 275-293. doi:10.1111/j.1360-0443.2012.04054.x Martinez, D., Gil, R., Slifstein, M., Hwang, D. R., Huang, Y., Perez, A., . . . Abi-Dargham, A. (2005). Alcohol dependence is associated with blunted dopamine transmission in the ventral striatum. *Biol Psychiatry,* 58(10), 779-786. doi:10.1016/j.biopsych.2005.04.044

McKee, S. A., Harrison, E. L., O'Malley, S. S., Krishnan-Sarin, S., Shi, J., Tetrault, J. M., . . . Balchunas, E. (2009). Varenicline reduces alcohol self-administration in heavy-drinking smokers. *Biological psychiatry,* 66(2), 185-190. doi:10.1016/j.biopsych.2009.01.029

Nutt, D. J., & Rehm, J. (2014). Doing it by numbers: a simple approach to reducing the harms of alcohol. *J Psychopharmacol,* 28(1), 3-7. doi:10.1177/0269881113512038

Palpacuer, C., Laviolle, B., Boussageon, R., Reymann, J. M., Bellissant, E., & Naudet, F. (2015). Risks and Benefits of Nalmefene in the Treatment of Adult Alcohol Dependence: A Systematic Literature Review and Meta-Analysis of Published and Unpublished Double-Blind Randomized Controlled Trials. *PLoS Med,* 12(12), e1001924. doi:10.1371/journal.pmed.1001924

Rehm, J. (2011). The risks associated with alcohol use and alcoholism. *Alcohol Res Health,* 34(2), 135-143. doi:Fea-AR& H-65 Fea-AR&H-65

Rehm, J., & Roerecke, M. (2013). Reduction of drinking in problem drinkers and all-cause mortality. *Alcohol Alcohol,* 48(4), 509-513. doi:10.1093/alcalc/agt021

Rose, J. E., & Behm, F. M. (2014). Combination treatment with varenicline and bupropion in an adaptive smoking cessation paradigm. *Am J Psychiatry,* 171(11), 1199-1205. doi:10.1176/appi.ajp.2014.13050595

Saunders, J. B., Aasland, O. G., Amundsen, A., & Grant, M. (1993). Alcohol consumption and related problems among primary health care patients: WHO collaborative project on early detection of persons with harmful alcohol consumption—I. *Addiction,* 88(3), 349-362.

Sobell, L. C., & Sobell, M. B. (1992). Timeline follow-back: a technique for assessing self-reported alcohol consumption, in Alcohol Consumption: Psychosocial and Biological Methods (Litten R Z, Allen J P eds.). *Human Press, Totowa, N.J.,* 31.

Socialstyrelsen. (2015). Nationella riktlinjer för vård och stöd vid missbruk och beroende. *Artikelnummer* 2015-4-2 Socialstyrelsen Riktlinjer. Retrieved from https://www.socialstyrelsen.se/Lists/Artikelkatalog/Attachments/19770/2015-4-2.pdf Soderpalm, B., & Ericson, M. (2013). Neurocircuitry involved in the development of alcohol addiction: the dopamine system and its access points. *Curr Top Behav Neurosci,* 13, 127-161. doi:10.1007/7854_2011_170

Soderpalm, B., Ericson, M., Olausson, P., Blomqvist, O., & Engel, J. A. (2000). Nicotinic mechanisms involved in the dopamine activating and reinforcing properties of ethanol. *Behav Brain Res,* 113(1-2), 85-96.

Soyka, M., & Chick, J. (2003). Use of acamprosate and opioid antagonists in the treatment of alcohol dependence: a European perspective. *Am J Addict,* 12 Suppl 1, S69-80.

Spagnolo, P. A., Ramchandani, V. A., Schwandt, M. L., Zhang, L., Blaine, S. K., Usala, J. M., . . . Heilig, M. (2014). Effects of naltrexone on neural and subjective response to alcohol in treatment-seeking alcohol-dependent patients. *Alcohol Clin Exp Res,* 38(12), 3024-3032. doi:10.1111/acer.12581

Srisurapanont, M., & Jarusuraisin, N. (2002). Opioid antagonists for alcohol dependence. *Cochrane Database Syst Rev*(2), CD001867. doi:10.1002/14651858.CD001867

Steensland, P., Simms, J. A., Holgate, J., Richards, J. K., & Bartlett, S. E. (2007). Varenicline, an alpha4beta2 nicotinic acetylcholine receptor partial agonist, selectively decreases ethanol consumption and seeking. *Proceedings of the National Academy of Sciences of the United States of America,* 104(30), 12518-12523. doi:10.1073/pnas.0705368104

True, W. R., Xian, H., Scherrer, J. F., Madden, P. A., Bucholz, K. K., Heath, A. C., . . . Tsuang, M. (1999). Common genetic vulnerability for nicotine and alcohol dependence in men. *Arch Gen Psychiatry,* 56(7), 655-661.

Vogeler, T., McClain, C., & Evoy, K. E. (2016). Combination bupropion SR and varenicline for smoking cessation: a systematic review. *Am J Drug Alcohol Abuse,* 42(2), 129-139. doi:10.3109/00952990.2015.1117480

Volkow, N. D., & Swanson, J. M. (2003). Variables that affect the clinical use and abuse of methylphenidate in the treatment of ADHD. *Am J Psychiatry,* 160(11), 1909-1918. doi:10.1176/appi.ajp.160.11.1909

Walther, L., de Bejczy, A., Lof, E., Hansson, T., Andersson, A., Guterstam, J., . . . Isaksson, A. (2015). Phosphatidylethanol is superior to carbohydrate-deficient transferrin and gamma-glutamyltransferase as an alcohol marker and is a reliable estimate of alcohol consumption level. *Alcohol Clin Exp Res,* 39(11), 2200-2208. doi:10.1111/acer.12883

Wang, G. J., Smith, L., Volkow, N. D., Telang, F., Logan, J., Tomasi, D., . . . Fowler, J. S. (2012). Decreased dopamine activity predicts relapse in methamphetamine abusers. *Mol Psychiatry,* 17(9), 918-925. doi:10.1038/mp.2011.86

WHO, W. H. o. (2014). Global Sataus Report on Alcohol and Health.

Wiesbeck, G. A., Weijers, H. G., Lesch, O. M., Glaser, T., Toennes, P. J., & Boening, J. (2001). Flupenthixol decanoate and relapse prevention in alcoholics: results from a placebo-controlled study. *Alcohol Alcohol,* 36(4), 329-334.

Wilens, T. E., Adler, L. A., Weiss, M. D., Michelson, D., Ramsey, J. L., Moore, R. J., . . . Atomoxetine, A. S. U. D. S. G. (2008). Atomoxetine treatment of adults with ADHD and comorbid alcohol use disorders. *Drug Alcohol Depend,* 96(1-2), 145-154. doi:10.1016/j.drugalcdep.2008.02.009

Zindel, L. R., & Kranzler, H. R. (2014). Pharmacotherapy of alcohol use disorders: seventy-five years of progress. *J Stud Alcohol Drugs Suppl,* 75 Suppl 17, 79-88.

Aubin, H. J., L. Karila and M. Reynaud, Pharmacotherapy for smoking cessation: present and future. Curr Pharm Des, 2011. 17(14): p. 1343-50. Review.

Bien, T. H., and R. Burge, Smoking and drinking: a review of the literature. Int J Addict, 1990. 25(12): p.1429-54.

Blomqvist O, Ericson M, Engel J A, Söderpalm B (1997) Accumbal dopamine overflow after ethanol: Localization of the antagonizing effect of mecamylamine. Eur J Pharmacol 334:149-156.

Blomqvist, O., et al., Voluntary ethanol intake in the rat: effects of nicotinic acetylcholine receptor blockade or subchronic nicotine treatment. Eur J Pharmacol, 1996. 314(3): p. 257-67.

Cardoso R A, Brozowski S J, Chavez-Noriega L E, Harpold M, Valenzuela C F, Harris R A (1999) Effects of ethanol on recombinant human neuronal nicotinic acetylcholine receptors expressed in Xenopus oocytes. J Pharmacol Exp Ther 289:774-780.

Coe, J. W., et al., Varenicline: an alpha4beta2 nicotinic receptor partial agonist for smoking cessation. J Med Chem, 2005. 48(10): p. 3474-7.

Corrigall W A, Coen K M, Adamson K L (1994) Self-administered nicotine activates the mesolimbic dopamine system through the ventral tegmental area. Brain Res 1653: 278-84.

de Bejczy, A., and B. Söderpalm, The effects of mirtazapine versus placebo on alcohol consumption in male high consumers of alcohol: a randomized, controlled trial. J Clin Psychopharmacol, 2015. 35(1): p. 43-50. December; 189(2): 201-10.

Einhorn, L. C., P. A. Johansen and F. J. White, Electrophysiological effects of cocaine in the mesoaccumbens dopamine system: studies in the ventral tegmental area. J Neurosci, 1988. 8(1): p. 100-12.

Ericson M, Blomqvist O, Engel J A, Söderpalm B (1998) Voluntary ethanol intake in the rat and the associated accumbal dopamine overflow are blocked by ventral tegmental mecamylamine. Eur J Pharmacol 358:189-196.

Ericson M, Löf E, Stomberg R, Chau P, Söderpalm B (2008) Nicotinic acetylcholine receptors in the anterior, but not posterior, ventral tegmental area mediate ethanol-induced elevation of accumbal dopamine levels. J Pharmacol Exp Ther 326:76-82.

Ericson, M., et al., Ethanol elevates accumbal dopamine levels via indirect activation of ventral tegmental nicotinic acetylcholine receptors. Eur J Pharmacol, 2003. 467: p. 85-93.

Feltmann, K., et al., The monoamine stabilizer (−)-OSU6162 counteracts downregulated dopamine output in the nucleus accumbens of long-term drinking Wistar rats. Addict Biol, 2016. 21: p. 438-49.

Heinz, A., et al., Correlation between dopamine D(2) receptors in the ventral striatum and central processing of alcohol cues and craving. Am J Psychiatry, 2004. 161(10): p. 1783-9.

Heinz, A., et al., Correlation of alcohol craving with striatal dopamine synthesis capacity and D2/3 receptor availability: a combined [18F]DOPA and [18F]DMFP PET study in detoxified alcoholic patients. Am J Psychiatry, 2005. 162(8): p. 1515-20.

Heinz, A., et al., Correlation of alcohol craving with striatal dopamine synthesis capacity and D2/3 receptor availability: a combined [18F]DOPA and [18F]DMFP PET study in detoxified alcoholic patients. Am J Psychiatry, 2005. 162(8): p. 1515-20.

Hillemacher, T., et al., Nicotine dependence is associated with compulsive alcohol craving. Addiction, 2006. 101(6): p. 892-7.

Larsson A, Edström L, Svensson L, Söderpalm B, Engel J A. Voluntary ethanol intake increases extracellular acetylcholine levels in the ventral tegmental area in the rat. Alcohol Alcohol. 2005 September-October; 40(5):349-58.

Larsson A, Jerlhag E, Svensson L, Söderpalm B, Engel J A. Is an alpha-conotoxin MII-sensitive mechanism involved in the neurochemical, stimulatory, and rewarding effects of ethanol? Alcohol. 2004 October-November; 34(2-3):239-50.

Larsson A, Svensson L, Söderpalm B, Engel J A. Role of different nicotinic acetylcholine receptors in mediating behavioral and neurochemical effects of ethanol in mice. Alcohol. 2002 November; 28(3):157-67.

Löf, E., et al., Nicotinic acetylcholine receptors in the ventral tegmental area mediate the dopamine activating and reinforcing properties of ethanol cues. Psychopharmacology, 2007. (Berl) 195: p. 333-343.

O'Malley S S, Zweben A, Fucito L M, Wu R, Piepmeier M E, Ockert D M, Bold K W, Petrakis I, Muvvala S, Jatlow P, Gueorguieva R. Effect of Varenicline Combined With Medical Management on Alcohol Use Disorder With Comorbid Cigarette Smoking: A Randomized Clinical Trial. JAMA Psychiatry. 2017 Dec. 20. doi:10.1001/jamapsychiatry.2017.3544. [Epub ahead of print] PubMed PMID: 29261824.

Picciotto M R, Zoli M, Rimondini R, Léna C, Marubio L M, Pich E M, Fuxe K, Changeux J P. Acetylcholine receptors containing the beta2 subunit are involved in the reinforcing properties of nicotine. Nature. 1998 Jan. 8; 391(6663):173-7.

Potthoff, A. D., G. Ellison and L. Nelson, Ethanol intake increases during continuous administration of amphetamine and nicotine, but not several other drugs. Pharmacol Biochem Behav, 1983. 18(4): p. 489-93.

Prochaska, J. J., K. Delucchi and S. M. Hall, A meta-analysis of smoking cessation interventions with individuals in substance abuse treatment or recovery. J Consult Clin Psychol, 2004. 72(6): p. 1144-56.

Rose, J. E. and F. M. Behm, Combination treatment with varenicline and bupropion in an adaptive smoking cessation paradigm. Am J Psychiatry, 2014. 171(11): p. 1199-205.

Smith, B. R., et al., Exposure to nicotine enhances acquisition of ethanol drinking by laboratory rats in a limited access paradigm. Psychopharmacology (Berl), 1999. 142 (4): p. 408-12.

Spanagel, R., and S. M. Hölter, Pharmacological validation of a new animal model of alcoholism. J Neural Transm (Vienna), 2000. 107(6): p. 669-80.

Volkow, N. D., et al., High levels of dopamine D2 receptors in unaffected members of alcoholic families: possible protective factors. Arch Gen Psychiatry, 2006. 63(9): p. 999-1008.

Volkow, N. D., et al., Profound decreases in dopamine release in striatum in detoxified alcoholics: possible orbitofrontal involvement. J Neurosci, 2007. 27(46): p. 12700-6.

Weiss, F., et al., Ethanol self-administration restores withdrawal-associated deficiencies in accumbal dopamine and 5-hydroxytryptamine release in dependent rats. J Neurosci, 1996. 16(10): p. 3474-85.

The invention claimed is:

1. A method of treating alcohol use disorder and/or treating alcohol risk consumption in a subject in need thereof, comprising administering to the subject a combination of from about 0.1 mg/day to about 5 mg/day of varenicline and from about 25 mg/day to about 600 mg/day of bupropion.

2. The method according to claim 1, wherein varenicline and bupropion are provided in a form which is suitable for sequential, separate and/or simultaneous administration.

3. The method according to claim 1, wherein administering comprises administering the varenicline and the bupropion sequentially to the subject.

4. The method according to claim 1, wherein administering comprises administering the varenicline and the bupropion simultaneously to the subject.

5. The method according to claim 1, wherein administering comprises administering the varenicline and the bupropion separately to the subject.

6. The method according to claim 1, wherein the varenicline is administered in an amount of from about 0.5 mg/day to about 2 mg/day.

7. The method according to claim 1, wherein the bupropion is administered in an amount of from about 150 mg/day to about 300 mg/day.

8. The method according to claim 1, wherein the subject is human.

9. The method according to claim 1, wherein the varenicline is administered in an amount of from about 0.5 mg/day to about 2 mg/day and the bupropion is administered in an amount of from about 150 mg/day to about 300 mg/day.

10. The method according to claim 1, wherein the subject is human.

* * * * *

UNITED STATES PATENT AND TRADEMARK OFFICE
CERTIFICATE OF CORRECTION

PATENT NO. : 11,318,143 B2
APPLICATION NO. : 16/484432
DATED : May 3, 2022
INVENTOR(S) : Bo Söderpalm et al.

It is certified that error appears in the above-identified patent and that said Letters Patent is hereby corrected as shown below:

On the Title Page

Item (30), change "1702590" to --1702590.9--.

Signed and Sealed this
Twenty-third Day of August, 2022

Katherine Kelly Vidal
*Director of the United States Patent and Trademark Office*